US012807913B2

(12) United States Patent
Trietsch et al.

(10) Patent No.: US 12,807,913 B2
(45) Date of Patent: Nov. 24, 2026

(54) MICROFLUIDIC CELL CULTURE DEVICE

(71) Applicant: Mimetas B.V., Oegstgeest (NL)

(72) Inventors: Sebastiaan Johannes Trietsch, Oegstgeest (NL); Arnaud Yannick Michel Nicolas, Oegstgeest (NL); Leonarda Jacoba Van Den Broek, Oegstgeest (NL); Bart Kramer, Oegstgeest (NL)

(73) Assignee: Mimetas B.V., Oegstgeest (NL)

( * ) Notice: Subject to any disclaimer, the term of this patent is extended or adjusted under 35 U.S.C. 154(b) by 881 days.

(21) Appl. No.: 18/004,671

(22) PCT Filed: Jul. 9, 2021

(86) PCT No.: PCT/EP2021/069205

§ 371 (c)(1),
(2) Date: Jan. 7, 2023

(87) PCT Pub. No.: WO2022/008733

PCT Pub. Date: Jan. 13, 2022

(65) Prior Publication Data

US 2023/0250377 A1 Aug. 10, 2023

(30) Foreign Application Priority Data

Jul. 9, 2020 (NL) ..................................... 2026038

(51) Int. Cl.
*C12M 3/06* (2006.01)
*C12M 1/00* (2006.01)
*C12M 3/00* (2006.01)

(52) U.S. Cl.
CPC ............ *C12M 23/16* (2013.01); *C12M 23/34* (2013.01); *C12M 23/38* (2013.01); *C12M 23/48* (2013.01)

(58) Field of Classification Search
CPC ...... C12M 23/16; C12M 23/34; C12M 23/38; C12M 23/48; C12M 23/12; C12M 35/04; B01L 2300/0681; B01L 2300/0829; B01L 2300/0864; B01L 3/502761
See application file for complete search history.

(56) References Cited

U.S. PATENT DOCUMENTS

| | | | | |
|---|---|---|---|---|
| 4,829,000 | A | 5/1989 | Kleinman | |
| 2011/0306122 | A1* | 12/2011 | Moritz | B01L 3/5085 435/325 |
| 2013/0084634 | A1* | 4/2013 | Hsu | C12M 25/01 435/325 |
| 2014/0106395 | A1* | 4/2014 | Fattinger | B01L 3/50853 435/32 |
| 2014/0335496 | A1 | 11/2014 | Sonia et al. | |
| 2015/0238952 | A1* | 8/2015 | Vulto | B01L 3/00 422/500 |
| 2021/0055283 | A1* | 2/2021 | Collins | C12M 41/48 |
| 2022/0017846 | A1* | 1/2022 | Vulto | C12M 35/04 |

FOREIGN PATENT DOCUMENTS

| | | | | |
|---|---|---|---|---|
| CN | 102257123 | A | 11/2011 | |
| CN | 103415616 | A | 11/2013 | |
| EP | 2811012 | A1 * | 12/2014 | C12M 25/01 |
| WO | WO 2010/031194 | A1 | 3/2010 | |
| WO | WO 2012/093173 | A1 | 7/2012 | |
| WO | 2012118799 | A2 | 11/2012 | |
| WO | 2013085909 | A1 | 6/2013 | |
| WO | 2014038943 | A1 | 3/2014 | |
| WO | 2017091075 | A1 | 6/2017 | |
| WO | 2017216113 | A2 | 12/2017 | |
| WO | 2019008189 | A1 | 1/2019 | |
| WO | 2019/153004 | A1 | 8/2019 | |
| WO | 2020109421 | A1 | 6/2020 | |

OTHER PUBLICATIONS

Dongeun Huh et al., Reconstituting Organ-Leval Lung Functions on a Chip, Science, 328, 1662, 2010.
Lee and Mooney, Hydrogels for Tissue Engineering (Chem Rev 2001;101(7):1869-1880).
Yurchenco (Quaranta) et al. Basal Lamina Assembly, 1994, Curr. Opin. Cell Biol. 6, 674-681, 1994).
Fahlenkamp, Cells and Culture Systems Used to Model the Small Airway Epithelium, Lung, 2016.
Sin, The Airway Epithelium: More Than Just a Structural Barrier, Therapeutic Advances in Respiratory Disease, 2011.
Guenat et al 2018—Medium throughput breathing human primary cell alveolus-on-a-chip model, Scientific Reports, www.nature.com/scientificreports.
Niklason 2015—A rotating bioreactor for scalable culture and differentiation of respiratory epithelium, Cell Medicine, vol. 7, pp. 109-121, 2015.
Qin 2018—A 3D human lung on a chip model for nanotoxicity testing, Toxicology Research, Royal Society of Chemistry.
Grego 2014—A biomimetic multicellular model of the airways using primary human cells, Lab on a Chip, Royal Society of Chemistry.
PCT Application No. PCT/EP2021/069205, International Search Report dated Oct. 18, 2021, 2 pages.
Chinese Office Action for Chinese Patent Application No. 202180048561.7, dated Aug. 6, 2026.

* cited by examiner

*Primary Examiner* — Lyle Alexander
*Assistant Examiner* — Alison Claire Gerhard
(74) *Attorney, Agent, or Firm* — Lathrop GPM LLP; Laura A. Labeots

(57) ABSTRACT

A microfluidic cell culture device is described. The device comprises a microfluidic network comprising a base, a microfluidic channel, and a cover, and at least one perfusion compartment and at least one support compartment inside the microfluidic channel. The base and cover each comprise an aperture, thereby defining a conduit through the microfluidic channel. The aperture is in fluidic contact with the at least one support compartment, and with the at least one perfusion compartment through the at least one support compartment. Methods for creating a fluid-fluid interface and for investigating a cellular response to a stimulant using the device are also described.

15 Claims, 15 Drawing Sheets

MICROFLUIDIC CELL CULTURE DEVICE

CROSS REFERENCE TO RELATED APPLICATIONS

This application is a national stage filing under 35 U.S.C. § 371 of International Patent Application No. PCT/EP2021/069205, filed Jul. 9, 2021, which claims priority to Netherlands Patent Application No. NL 2026038, filed Jul. 9, 2020 and granted Mar. 15, 2022. The contents of the above patent applications are incorporated herein by reference in their entireties.

FIELD OF THE INVENTION

The present invention relates to a microfluidic cell culture device, and to methods of creating fluid-fluid interfaces and for investigating cellular responses to stimulants using the microfluidic device.

BACKGROUND OF THE INVENTION

In a drive towards simulating ever more physiologically relevant conditions in cell culture, numerous models have been developed to simulate, for example, perfusion flow, and co-culture in pre-clinical cell-based models for assessing drug efficacy and/or ADME safety.

Microfluidics has become a popular platform technology for such in vitro cell culture models due to the inherent flow of liquids or media during use, along with advances in microengineering techniques that facilitate and enable fabrication of complex microfluidic networks. However, there is still much interest in generating models that simulate or reproduce the cellular environment in the different organs of the human or animal body.

Challenges remain in translating key characteristics of the lungs into a high throughput model. Airway epithelium is responsible for the uptake of oxygen in blood and thereby supports all cells in the human body. These airway epithelial cells are apically in contact with outside air and basolaterally connected to the underlying interstitium from which nutrients are obtained. The lungs also form a physical barrier to the interior milieu and are the first line of defense against inhaled particles and/or pathogens that get trapped in a protecting mucus layer.

Creation of a high throughput lung model would allow for rapid testing of potential therapeutic agents to target, for example, viral or bacterial infections of the lungs, while creation of a high throughput gut model has equal importance for understanding drug absorption as well as therapeutic activity. There exists a need for improved devices and methods for simulating real-life cellular environments in vitro.

SUMMARY OF THE INVENTION

In a first aspect of the invention there is provided a microfluidic device, comprising:

- a microfluidic network, the microfluidic network comprising:
  - a base, a microfluidic channel, and a cover;
  - at least one perfusion compartment inside the microfluidic channel; and
  - at least one support compartment inside the microfluidic channel;

wherein

- the base and cover each comprise an aperture, thereby defining a conduit through the microfluidic channel; and
- the conduit is in fluidic contact with the at least one support compartment, and in fluidic contact with the at least one perfusion compartment through the at least one support compartment.

In a second aspect of the invention there is provided a method of creating a fluid-fluid interface in a microfluidic cell culture device comprising a microfluidic network having a base, a microfluidic channel, and a cover, with at least one perfusion compartment and at least one support compartment inside the microfluidic channel, and the base and cover each comprising an aperture thereby defining a conduit through the microfluidic channel; the method comprising:

- introducing a support scaffold into the at least one support compartment so as to form a scaffold surface facing the conduit;
- introducing a medium containing cells into the conduit via the aperture in the cover while preventing flow of the medium from the conduit via the aperture in the base;
- allowing the cells to form into a layer on the scaffold surface; and
- removing the medium from the conduit to expose the cells.

According to a third aspect of the present invention, there is provided an assay plate, comprising the device of the first aspect provided with a support scaffold within the support compartment of the microfluidic channel, optionally wherein the support scaffold comprises one or more cells or cell aggregates, preferably lining its surface facing the conduit.

In a fourth aspect of the invention there is provided a method of investigating a cellular response to a stimulant, comprising:

- creating a fluid-fluid interface in a microfluidic device according to the method of the second aspect; and
- subjecting the exposed cells to a fluid stream by directing the fluid stream through the conduit.

In a fifth aspect of the invention there is provided a method of investigating a cellular response to a stimulant, comprising:

- using the assay plate of the third aspect; and
- subjecting the exposed cells to a fluid stream by directing the fluid stream through the conduit.

Other preferred embodiments are defined in the description and dependent claims which follow.

Previous studies have attempted to create a lung model in a cell culture environment. However, creating the air-liquid interface without dislodging seeded cells and then supplying the seeded cells with nutrients in a high throughput manner has hitherto proved challenging. A device in accordance with any of the afore-mentioned aspects unexpectedly enables the creation of an air-liquid interface in a lung model, thus opening up the development of improved in vitro or ex vivo model systems for assessing drug efficacy or ADME safety.

Definitions

Various terms relating to the devices, methods, uses and other aspects of the present invention are used throughout the specification and claims. Such terms are to be given their ordinary meaning in the art to which the invention pertains, unless otherwise indicated. Other specifically defined terms are to be construed in a manner consistent with the definition provided herein. Although any methods and materials similar or equivalent to those described herein can be used in the practice for testing of the present invention, the preferred materials and methods are described herein.

As used herein, the "a," "an," and "the" singular forms also include plural referents unless the content clearly dictates otherwise. Thus, for example, reference to "a cell" includes a combination of two or more cells, and the like.

As used herein, "substantially", "about" and "approximately" when referring to a measurable value such as an amount, a temporal duration, and the like, are meant to encompass variations of ±20% or ±10%, more preferably ±5%, even more preferably +1%, and still more preferably ±0.1% from the specified value, as such variations are appropriate to perform the disclosed methods.

As used herein, "comprising" is construed as being inclusive and open ended, and not exclusive. Specifically, the term and variations thereof mean the specified features, steps or components are included. These terms are not to be interpreted to exclude the presence of other features, steps or components.

As used herein, "exemplary" means "serving as an example, instance, or illustration," and should not be construed as excluding other configurations disclosed herein.

As used herein, the term "microfluidic channel" refers to a channel on or through a layer of material that is covered by a top-substrate or cover, or to a channel underneath or through a material placed onto a bottom substrate or base, with at least one of the dimensions of length, width or height being in the sub-millimeter range. It will be understood that the term encompasses channels which are linear channels, as well as channels which are branched, or have bends or corners within their path. A microfluidic channel typically comprises an inlet for administering a volume of liquid. The volume enclosed by a microfluidic channel is typically in the microliter or sub-microliter range. A microfluidic channel typically comprises a base, which may be the top surface of an underlying material, two side walls, and a ceiling, which may be the lower surface of a top substrate or cover overlying the microfluidic channel, with any configuration of inlets, outlets and/or vents as required. The base, side walls and ceiling may each be referred to as an inner surface of the microfluidic channel, and collectively may be referred to as the inner surfaces. In some examples, the microfluidic channel may have a circular or semi-circular cross-section, which would then be considered to have one or two inner surfaces respectively.

As used herein, "droplet retention structures", and "capillary pressure barriers" are used interchangeably, and are used in reference to features of a device that keep a liquid-air meniscus pinned on a certain position by capillary forces. A capillary pressure barrier can be considered to divide a microfluidic channel having a volume $V_0$ into two sub-volumes $V_1$ and $V_2$ into which different fluids can be introduced. Put differently, a capillary pressure barrier at least partially defines a sub-volume or sub-volumes of a microfluidic channel by being located at the boundary between two sub-volumes.

As used herein, with particular reference to capillary pressure barriers, a "closed geometric configuration" is one in which the capillary pressure barrier is other than a linear capillary pressure barrier with two ends and instead forms a closed loop. For example, when viewed from above, a capillary pressure barrier with a closed geometric configuration may comprise a circular capillary pressure barrier, or a polygonal capillary pressure barrier, for example a triangular capillary pressure barrier, or a square capillary pressure barrier, or a pentagonal capillary pressure barrier, and so on. In some examples, a closed geometric configuration of capillary pressure barrier may also refer to two linear capillary pressure barriers arranged so as to both intersect with the same wall or walls of the microfluidic channel and thereby close off or define an area of the microfluidic channel bounded by the two linear capillary pressure barriers and the wall(s). As used herein, the term "concentric" is to be understood as referring to any closed geometric configuration and not solely to a circular configuration. For example, the term "concentric" may also be understood as referring to two squares of the same or different dimensions which are aligned so that the centre of one square is aligned with the centre of the other square.

As used herein, a "linear" capillary pressure barrier is not to be construed as being a straight line, but is instead to be construed as being other than a closed geometric configuration, i.e. as a line with two ends, but which may comprise one or more bends or angles. A linear capillary pressure barrier typically intersects at each end with a side-wall or inner surface of the microfluidic channel.

As used herein, the term "endothelial cells" refers to cells of endothelial origin, or cells that are differentiated into a state in which they express markers identifying the cell as an endothelial cell.

As used herein, the term "epithelial cells" refers to cells of epithelial origin, or cells that are differentiated into a state in which they express markers identifying the cell as an epithelial cell.

As used herein, the term "droplet" refers to a volume of liquid that may or may not exceed the height of the microfluidic channel and does not necessarily represent a round, spherical shape. For example, references to a gel droplet are to a volume of gel in the support compartment.

As used herein, the term "biological tissue" refers to a collection of identical, similar or different types of functionally interconnected cells that are to be cultured and/or assayed in the methods described herein. The cells may be a cell aggregate, or a particular tissue sample from a patient. For example, the term "biological tissue" encompasses organoids, tissue biopsies, tumor tissue, resected tissue material, spheroids and embryonic bodies.

As used herein, the term "cell aggregate" refers to a 3D cluster of cells in contrast with surface attached cells that typically grow in monolayers. 3D clusters of cells are typically associated with a more in-vivo like situation. In contrast, surface attached cells may be strongly influenced by the properties of the substrate and may undergo de-differentiation or undergo transition to other cell types.

As used herein, the term "lumened cellular component" refers to a biological tissue (i.e. constituted of cells) having a lumen, for example a microvessel having apical and basal surfaces.

BRIEF DESCRIPTION OF THE FIGURES

The present invention will now be described by way of example only, with reference to the Figures, in which.

DETAILED DESCRIPTION OF THE INVENTION

Microfluidic Device

Figure 1:
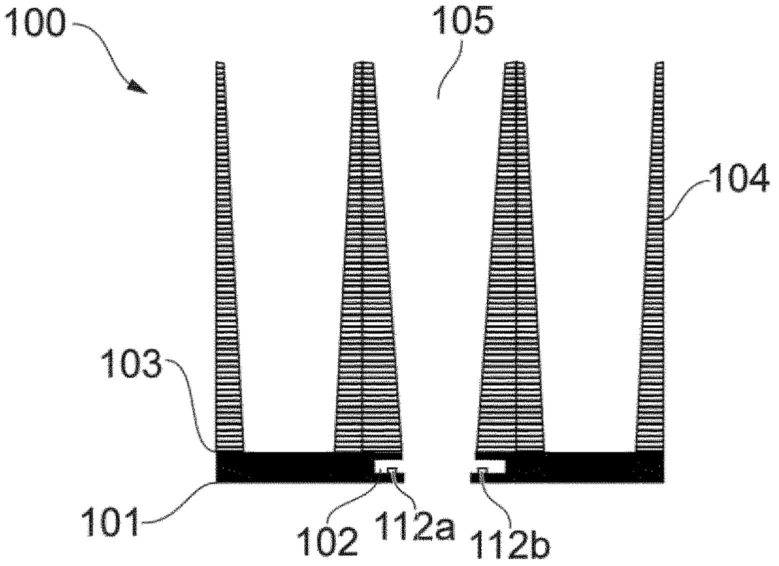
FIG. 1 shows a vertical cross-section view of a first exemplary configuration for a microfluidic network as used in a device as herein described.

A microfluidic device is described. The microfluidic device is preferably in a multi-array format/multi-well format to enable its use in in-vitro cell-based assays, pharmaceutical screening assays, toxicity assays, and the like; in particular in a high-throughput screening format. Such multi-well culture plates are available in 6-, 12-, 24-, 48-, 96-, 384- and 1536 sample wells arranged in a rectangular matrix, wherein in the context of the present invention a multi-array configuration of microfluidic networks as herein described are present in the microfluidic device. In one example, the microfluidic device is compatible with one or more dimensions of the standard ANSI/SLAS microtiter plate format. In an alternative embodiment the microfluidic device is in a multi-array format with dimensions of a microscope glass slide. In some examples, the microfluidic device is provided with one or more functions including one or more electrodes for conducting electrical experiments; transparent materials, windows or other modification to enable optical measurements to be taken, and so on.

The microfluidic device therefore preferably has a plurality of microfluidic networks as herein described. In one example, the plurality of microfluidic networks are fluidly disconnected from each other; in other words, each microfluidic network operates independently of any other microfluidic network present on the microfluidic device. In other examples, as will be described later, the microfluidic networks may be connected by one or more connecting channels.

Generally, the microfluidic device is a microfluidic device that comprises at least a microfluidic network having a microfluidic channel. Different configurations of microfluidic channels or networks are possible within the metes and bounds of the invention, but may include for example a volume or sub-volume within or in fluid communication with the microfluidic channel, for receiving and confining a gel, for example an extracellular matrix.

The microfluidic device generally comprises a microfluidic network, which will now be described in detail.

Microfluidic Network

The microfluidic network of the microfluidic device generally comprises a base, a microfluidic channel or microfluidic layer and a cover, also referred to herein as a cover layer, and can be fabricated in a variety of manners.

The base, also referred to herein as the base layer, or bottom substrate, is preferably formed from a substantially rigid material, such as glass or plastic, and serves to provide a supporting surface for the rest of the microfluidic network. In one example, the base is of the same or similar dimensions to the well area of a standard ANSI/SLAS microtitre plate. In some examples, the base comprises an aperture to the microfluidic layer or channel of the microfluidic network. In some examples, the base comprises a connecting channel disposed therein. The connecting channel connects a microfluidic network to at least one other microfluidic network of the microfluidic device as described herein via the aperture in the base. In some examples, the connecting channel is connected to the conduit of a microfluidic network by way of a fluidic inlet to the aperture in the base so as to allow a flow of fluid through the conduit.

The microfluidic device or network comprises a microfluidic channel or microfluidic layer disposed on the base. In some examples, the microfluidic channel may comprise or be divided into sub-volumes, for example by the presence of a capillary pressure barrier as described herein. In some examples, the microfluidic channel may comprise a first sub-volume, which may be referred to as a support compartment. In some examples, the support compartment may be defined in part by the presence of a capillary pressure barrier and/or the rim of the aperture in the base.

In some examples, the microfluidic channel further comprises a second sub-volume comprising a flow channel or perfusion compartment. In some examples, the perfusion compartment of the second sub-volume is an in-use flow channel.

A typical method of fabrication of a microfluidic channel is to cast a mouldable material such as polydimethylsiloxane onto a mould, so imprinting the microfluidic channel into the silicon rubber material thereby forming a microfluidic layer. The rubber material with the channel embedded is subsequently placed on a base layer of glass or of the same material to thus create a seal. Alternatively, the channel structure could be etched in a material such as glass or silicon, followed by bonding to a top or bottom substrate (also referred to herein as a cover layer and base layer). Injection moulding or embossing of plastics followed by bonding is another manner to fabricate the microfluidic channel network. Yet another technique for fabricating the microfluidic channel network is by photo lithographically patterning the microfluidic channel network in a photopatternable polymer, such as SU-8 or various other dry film or liquid photoresists, followed by a bonding step. When referred to bonding it is meant the closure of the channel by a cover or base. Bonding techniques include anodic bonding, covalent bonding, solvent bonding, adhesive bonding, and thermal bonding amongst others.

As deduced from the various fabrication methods above, the microfluidic layer may comprise a sub-layer comprising a microfluidic channel disposed on the base layer, or is patterned in either the cover or base layer. In an in use orientation, the microfluidic sub-layer is disposed on the top surface of the base layer. The microfluidic channel may be formed as a channel through a sub-layer of material disposed on the base layer. In one example, the material of the sub-layer is a polymer placed on the base layer and into which the microfluidic channel is patterned. In some examples, the microfluidic layer comprises two or more microfluidic channels, which may be in fluidic communication with each other.

The microfluidic network comprises a cover or cover layer covering the microfluidic channel. The cover or cover layer can be formed from any suitable material as is known in the art, for example a glass layer bonded to the sub-layer comprising the microfluidic channel. In one example, the cover layer is provided with pre-formed holes or apertures at defined points. In some examples an aperture in the cover is substantially aligned with an aperture in the base. In some examples, a connecting channel is provided in the cover, connecting the conduits of at least two microfluidic networks of the plurality of microfluidic networks via their respective apertures in the cover. In some examples, the connecting channel is connected to the conduit of a microfluidic network by way of a fluidic inlet to the aperture in the cover so as to allow a flow of fluid through the conduit. The apertures in the cover and base allow for fluid communication between the microfluidic channel of the microfluidic layer and other components of the microfluidic device disposed thereon or thereunder. In general, the apertures fulfil the function as interface with the outside world or wells disposed on top of the cover. In some examples, the apertures in the cover and base are configured to function as capillary pressure barriers. For example, the apertures in the cover and base have rims, which can function as capillary pressure barriers to pin a liquid and prevent the liquid from flowing through the apertures.

In some examples, the cover comprises a connecting channel disposed therein. The connecting channel connects a microfluidic network to at least one other microfluidic network of the microfluidic device as described herein through the aperture in the cover. In this way, for example, each microfluidic network can be individually provided with a candidate drug via the perfusion channel, but all microfluidic networks can then be provided with the same fluid stream via the connecting channel to the individual conduits. In some examples, a connecting channel is provided in the base and a second connecting channel is provided in the cover, providing one or more fluidic inlets and/or outlets to the apertures in the base and cover so as to allow fluid flow through the conduit of a microfluidic network. In some examples, the connecting channels providing one or more fluidic inlets and/or outlets to the apertures in the base and cover so as to allow fluid flow through the conduits of a plurality of microfluidic networks.

The microfluidic channel may be provided with one or more fluid inlets, and one or more outlets or vents, as required for any particular use of the microfluidic network of the microfluidic device. In order to allow filling, emptying and perfusion of a fluid through the microfluidic network, the microfluidic channel is preferably provided with at least one inlet and at least one outlet or vent. In one example, each of the at least one inlet and at least one outlet or vent is preferably a pre-formed aperture in the cover layer. It will be understood that there typically is no geometrical distinction between an in—and outlet and that in many cases they can be used as in—or outlet interchangeably.

In some examples, the microfluidic device further comprises a top layer disposed on the above mentioned cover layer, the top layer having one, or at least one well or reservoir in fluidic communication with the rest of the microfluidic device. In some examples, the top layer has a plurality of such wells, and at least one, for example at least two, for example at least three wells are in communication with a microfluidic network or channel of the device. For example, the top layer may comprise a well or reservoir in fluidic communication with a microfluidic network via an inlet aperture provided in a cover layer of the microfluidic network thereby forming a SLAS compliant wellplate. In some examples, the top layer having at least one well and the microfluidic layer are integrally formed. For example, a microfluidic channel may be patterned onto the underside of an injection moulded microtiter plate having at least one well.

Support Compartment

The microfluidic channel comprises at least one support compartment. References herein to a support compartment will be understood as being to the at least one support compartment and as being generally applicable to more than one support compartment. The support compartment may be generally disposed within the microfluidic channel in proximity to the apertures in the base and in the cover. In some examples, the support compartment is disposed within the microfluidic channel between the perfusion compartment and a conduit formed by the apertures in the base and in the cover. In the context of the present disclosure, the support compartment is to be understood as being a region of the microfluidic channel which is open to and in fluidic communication with other components of the microfluidic device, for example the perfusion channel and conduit. Thus, while the support compartment may be defined in part by the inner surfaces of the microfluidic channel (e.g. two side walls and top and bottom substrates), it is to a lesser or greater degree "open" to the other regions of the microfluidic channel and other regions of the device, with its boundaries being defined as set out below.

In some examples, the support compartment is defined at least in part by one or more of the aperture in the base, the aperture in the cover and a capillary pressure barrier located in the microfluidic channel. In some examples, the apertures in the base and in the cover function as capillary pressure barriers to pin or confine a fluid within the support compartment without overflow through either aperture. In some examples, the support compartment comprises a capillary pressure barrier defining a boundary between the support compartment and the perfusion compartment. In this way, a fluid within the support compartment can be confined therein and not overflow into the perfusion compartment. It will of course be understood that the capillary pressure barrier is not a structure that completely seals the microfluidic channel so as to prevent all fluid flow between the support compartment and perfusion compartment. Instead, the capillary pressure barrier functions to control the position of a fluid meniscus through meniscus pinning and thereby delineates the different regions of the microfluidic channel.

In some examples, the support compartment comprises an inlet and an outlet, which may be immediately adjacent the support compartment. In some examples, the inlet and outlet are spatially separated from the support compartment and linked by a flow channel.

In some examples, the support compartment is defined as the region of the microfluidic channel delimited by the apertures in the base and cover, and a capillary pressure barrier within the microfluidic channel. In some examples, the support compartment does not comprise a membrane. In other examples, the support compartment comprises a porous membrane, which may have a gel disposed in the pores of the membrane. In yet other examples, the support compartment does not comprise a membrane but is configured to receive a gel or gel-precursor. The gel or gel-precursor may be as described herein, and may for example be a gel comprising an extra-cellular matrix capable of supporting cells.

In some examples, the support compartment provides or contains the structural support or support scaffold to allow a layer of cells or cell aggregates to form so as to create a fluid-fluid interface. In some examples, the support compartment is configured to receive and confine a gel therein so as to form a layer of cells or cell aggregates on a surface of the gel facing a conduit, with the gel performing the function of the support scaffold. In some examples, the support compartment comprises a porous membrane having a gel disposed within its pores, and the cells or cell aggregates form a layer on the surface of the gel-containing porous membrane with the combination of the membrane and gel performing the function of the support scaffold. The support compartment with gel thus provides the structural and functional support to a layer of cells, by providing a surface on which the cells can grow and by allowing flow of nutrients through the gel to the cells.

In some examples, the support compartment provides an initial structural support to seeded cells through a gel or other extracellular matrix present in the support compartment until a time that the cells have been cultured enough that the support is no longer required. In these examples, the gel or other extracellular matrix may be a sacrificial or degradable material that over time degrades to leave a cell tubule supported by itself. Thus, the cultured cells in some examples in and of themselves provide a structural network within the support compartment to separate the perfusion channel and the conduit and so enhance the structural integrity or function of the support scaffold. These examples enable formation of a direct air-air interface, or a direct air-liquid interface as may be required.

In some examples, the microfluidic channel comprises more than one support compartment. For example, the microfluidic channel may comprise one support compartment either side of the apertures formed in the cover and in the base. Each support compartment may be in fluid communication with its own reservoir for fluid supply, or each support compartment may be in fluid communication with a common reservoir for fluid supply.

Perfusion Compartment

The microfluidic channel comprises at least one perfusion compartment. References herein to a perfusion compartment will be understood as being to the at least one perfusion compartment and as being generally applicable to more than one perfusion compartment. The perfusion compartment may be generally disposed within the microfluidic channel in proximity to the support compartment. In some examples, the perfusion compartment is disposed within the microfluidic channel with the support compartment disposed between the perfusion compartment and a conduit formed by the apertures in the base and in the cover. In some examples, the perfusion compartment and the support compartment are adjacent one another and in the same plane in the microfluidic network.

In some examples, the perfusion compartment is defined at least in part by one or more capillary pressure barriers located in the microfluidic channel. In some examples, the one or more capillary pressure barriers define a boundary for controlling (but not preventing) fluid flow between the support compartment and the perfusion compartment. In this way, the meniscus of a fluid within the support compartment can be pinned at the capillary pressure barrier so as to be confined therein and not overflow into the perfusion compartment and vice versa. It will be understood that pinning of a first liquid in the support compartment and introduction of a second liquid into the perfusion compartment would result in coalescence of the two menisci, and fluid flow between the support and perfusion compartments. Thus, the one or more capillary pressure barriers are used to control, but not completely prevent, fluid flow within the microfluidic channel.

In some examples, the perfusion compartment comprises an inlet and an outlet, which may be immediately adjacent the perfusion compartment. In some examples, the inlet and outlet are spatially separated from the perfusion compartment and linked by a flow channel.

In some examples, the perfusion compartment is configured to provide a flow of nutrients to the support compartment to allow a layer of cells or cell aggregates to form and grow so as to create a fluid-fluid interface.

In some examples, the perfusion compartment is configured to receive media containing one or more types of cells or cell aggregates so as to form a layer of cells or cell aggregates on a surface of the perfusion compartment. In some examples, the perfusion compartment is configured to receive media containing one or more types of cells or cell aggregates so as to form a layer of cells on a surface of the support compartment adjacent the perfusion compartment.

In some examples, the one or more types of cells or cell aggregates may be selected from: epithelial or endothelial cells for lining the perfusion compartment, potentially forming a tube or blood vessel; epithelial or endothelial cells to be situated inside a gel, extracellular matrix or scaffold, preferably forming lumened structures, more preferably forming a vascular bed; stromal cells in or on a gel, extracellular matrix or scaffold; muscle cells in or on a gel, extracellular matrix or scaffold; or any other type of cell that may be required to create a desired in vitro model system.

In some examples, the microfluidic channel comprises more than one perfusion compartment. For example, the microfluidic channel may comprise one perfusion compartment either side of the apertures formed in the cover and in the base. Each perfusion compartment may be in fluid communication with its own reservoir for fluid supply, or each perfusion compartment may be in fluid communication with a common reservoir for fluid supply.

Apertures

As described herein, the base layer and cover layer each comprise an aperture. The apertures may be apertures to the microfluidic layer of the device. In some examples, the apertures are substantially aligned with one another. In some examples, the apertures are substantially concentric with one another. In some examples, the apertures are arranged so as to define a conduit running through the microfluidic device.

In one example, the diameter or area defined by the aperture in the cover is greater than the diameter or area defined by the aperture in the base; in other words, the cover aperture is circumferential to and larger than the base aperture- or the diameter of the aperture in the base is smaller than the diameter of the aperture in the cover. In another example, the diameter or area defined by the circumference of the aperture in the base is greater than the diameter or area defined by the circumference of the aperture in the cover; in other words the aperture in the base is circumferential to and larger than the aperture in the cover. Irrespective of the shapes, one or both of the base and cover apertures may define the permitted contact area of a liquid or gel composition introduced into the support compartment.

In some examples, the aperture in the base is smaller than the aperture in the cover so that the defined conduit has a frusto-conical cross-section tapering toward the base. In this example, a gel within the support compartment will have a surface facing the conduit which slopes down to the aperture in the base, thereby providing a non-vertical surface on which a layer of cells can form.

In some examples, the aperture in the base and the aperture in the cover each have a diameter or largest dimension of no more than about 2 mm, for example less than about 1.5 mm, for example less than about 1 mm, for example less than about 500 μm, for example to about 250 μm. In some examples, the aperture in the base and the aperture in the cover each have a diameter or largest dimension of about 1 mm or 500 μm. In some examples, the aperture in the base has a diameter of 1 mm or 500 μm and the aperture in the cover has a diameter or largest dimension of 1 mm. The aperture in the base is preferably of a dimension that it is small enough to form a stable capillary pressure barrier, but large enough to prevent filling up through interstitial flow, for example a diameter of no more than about 500 μm.

In some examples, one or both of the base and cover apertures may define the permitted contact area of a liquid or gel composition introduced into the support compartment by functioning as capillary pressure barriers. In some examples, the rim of an aperture may be configured to function as a capillary pressure barrier without further modification. In some examples, the rim of an aperture may comprise a raised section in the form of a lip extending into the microfluidic channel which functions as a capillary pressure barrier. Other configurations of capillary pressure barrier formed at the rim of an aperture are contemplated, such as those described herein.

In some examples, the aperture in the base is configured to function as a capillary pressure barrier so as to prevent liquid introduced into the conduit from flowing through the aperture and into the base. In this way, media containing cells can be introduced into the conduit via the aperture in the cover without loss of media (and cells) through the aperture in the base.

Conduit

As described herein, the base layer and cover layer each comprise an aperture. In some examples, the apertures are arranged as described herein so as to define a conduit extending through the microfluidic device. In some examples, the conduit is perpendicular or orthogonal to the plane of the microfluidic layer. For example, in an in-use orientation, the microfluidic layer may be in a substantially horizontal orientation and the conduit may be in a substantially vertical orientation. It will be understood that the apertures may be offset from one another so as to define a conduit at an oblique angle to the plane of the microfluidic layer. In some examples, the conduit is frusto-conical in cross section, for example by tapering toward the aperture in base. A conduit having this form is advantageous for an initial seeding, due to the tapering of the gel surface, and for imaging of the seeded surface during subsequent experiments.

In some examples, the conduit is configured to receive a flow of fluid, for example air, gas or liquid via the aperture in the cover and/or the aperture in the base. The fluid flow may be via a well or reservoir disposed above the aperture in the cover. The fluid flow may be via one or more inlets or outlets of the device that are in fluid communication with the aperture. The device may generally be configured to connect to a supply of fluid (for example compressed air or gas, or a flow of dispersed particles). For example, the device may be configured to connect to a removable manifold to provide a fluid flow to the conduit or conduits of one or more microfluidic networks. In some examples, the manifold may have one or more branches from a single fluid inlet to connect a single fluid supply to each conduit of a plurality of microfluidic networks. In some examples, the manifold may have one or more branches to connect a plurality of fluid supplies to the conduit of a single microfluidic network. In some examples, the device may be configured to connect to more than one manifold, each with a branched flow path as described above, with the flow path of one manifold terminating at the cover aperture of a microfluidic network and the flow path of the second manifold terminating at the base aperture of the microfluidic network. The supply of fluid includes a supply of positive or negative pressure, resulting in a flow in one direction or the other depending on the nature of the pressure. Thus, fluid flow through the conduit in both directions can be achieved.

Capillary Pressure Barrier

The microfluidic network of the microfluidic device may comprise a capillary pressure barrier.

In some examples, the capillary pressure barrier is substantially aligned with an aperture in the cover. In some examples, the capillary pressure barrier divides the microfluidic channel into a first sub-volume and a second sub-volume, for example into a perfusion compartment and a support compartment, or a support compartment and a conduit. In some examples, the capillary pressure barrier at least partially defines a sub-volume of the microfluidic channel.

The function and patterning of capillary pressure barriers have been previously described, for example in WO 2014/038943 A1. As will become apparent from the exemplary embodiments described hereinafter, the capillary pressure barrier, also referred to herein as a droplet retention structure, is not to be understood as a wall or a cavity which can for example be filled with a liquid, but consists of or comprises a structure which ensures that such a droplet does not spread due to the surface tension. This concept is referred to as meniscus pinning. As such, stable confinement of a liquid to a region of a microfluidic channel of the device, for example a support compartment can be achieved. In one example, the capillary pressure barrier may be referred to as a confining phaseguide, which is configured to not be overflown during normal use of the cell culture device or during initial filling of a cell culture device with a first liquid. The nature of the confinement of a liquid is described later in connection with the description of the methods of the present invention. In some examples, an aperture can function as a capillary pressure barrier. For example, an aperture in the base can function as a capillary pressure barrier to pin a liquid, or an aperture in the cover can function as a capillary pressure barrier.

In one example, the capillary pressure barrier comprises or consists of a rim or ridge of material protruding from an internal surface of the microfluidic channel; or a groove in an internal surface of the microfluidic channel. The sidewall of the rim or ridge may have an angle $\alpha$ with the top of the rim or ridge that is preferably as large as possible. In order to provide a good barrier, the angle α should be larger than 70°, typically around 90°. The same counts for the angle α between the sidewall of the ridge and the internal surface of the microfluidic channel on which the capillary pressure barrier is located. Similar requirements are placed on a capillary pressure barrier formed as a groove.

An alternative form of capillary pressure barrier is a region of material of different wettability to an internal surface of the microfluidic channel, which acts as a spreading stop due to capillary force/surface tension. In one example, the internal surfaces of the microfluidic channel comprise a hydrophilic material and the capillary pressure barrier is a region of hydrophobic, or less hydrophilic material. In one example, the internal surfaces of the microfluidic channel comprise a hydrophobic material and the capillary pressure barrier is a region of hydrophilic, or less hydrophobic material.

In one example, the capillary pressure barrier is selected from a rim or ridge, a groove, a hole, or a hydrophobic line of material or combinations thereof. In other examples, capillary pressure barriers can be created by a widening of the microfluidic channel or by pillars at selected intervals, the arrangement of which can define the support compartment that is to be occupied by the gel. In one example, the pillars extend the full height of the microfluidic channel.

As a result of the presence of a capillary pressure barrier, liquid is prevented from flowing beyond the capillary pressure barrier and enables the formation of stably confined volumes in the microfluidic channel, for example in one or more of the first, second or third sub-volumes, any of which may be referred to or function as a support compartment, a perfusion compartment or a conduit.

In one example, the capillary pressure barrier is located on an underside of the cover layer and is spaced from the aperture. In one example, the capillary pressure barrier is provided on the base of the microfluidic layer or on the internal surface of the microfluidic channel opposite or facing an aperture in the cover. In one example, the capillary pressure barrier is located on the base layer and is spaced from the aperture. In one example, the capillary pressure barrier is present as previously defined in order to confine a droplet of fluid to a sub-volume of the microfluidic layer aligned with an aperture of the cover.

In one example, the capillary pressure barrier defines at least in part a surface, for example a floor, of a first sub-volume of the microfluidic channel which may also be referred to as a support compartment. The capillary pressure barrier is configured to confine a fluid to the first sub-volume of the microfluidic channel. In one example, the capillary pressure barrier comprises a closed geometric configuration. In one example, the capillary pressure barrier is concentric with the aperture of the cover layer.

In one example, the capillary pressure barrier is a substantially linear capillary pressure barrier which spans the complete width of the microfluidic channel and intersects on each end with sidewalls of the microfluidic channel.

Second Capillary Pressure Barrier

In some examples, the microfluidic network of the device is provided with a second capillary pressure barrier, the form and function of which is substantially as described above. For the avoidance of doubt, references to "a capillary pressure barrier" are to be understood as references to "the first capillary pressure barrier" when a second capillary pressure barrier is present in the device. In some examples, the second capillary pressure barrier is configured and located so as to restrict spread of a droplet of fluid within the microfluidic network, for example within the support compartment.

In one example, the second capillary pressure barrier is provided on an internal surface of the microfluidic channel. For example, the second capillary pressure barrier is present on the base of the microfluidic layer on the internal surface of the microfluidic channel, or on the cover of the microfluidic layer on the internal surface of the microfluidic channel. In one example, the second capillary pressure barrier is present as previously defined to confine a droplet of fluid to the region of the microfluidic layer aligned with the aperture.

In one example, the second capillary pressure barrier defines at least in part, in combination with the first capillary pressure barrier, a surface of the support compartment on the base of the microfluidic channel. The second capillary pressure barrier is configured, in combination with the first capillary pressure barrier, to confine a fluid to the support compartment.

In one example, the second capillary pressure barrier is a substantially linear capillary pressure barrier which spans the complete width of the microfluidic channel and intersects on each end with sidewalls of the microfluidic channel. In this example, the first and second capillary pressure barriers in conjunction with the walls with which they intersect may define an area which is aligned with the aperture of the cover layer, and which may also be concentric with the aperture of the cover. Alternatively, or in addition, the first and second capillary pressure barriers in conjunction with the walls with which they intersect may define an area which is aligned with the aperture of the base layer, and which may also be concentric with the aperture of the base. In these examples, the first capillary pressure barrier can be considered as dividing the microfluidic network into a first sub-volume comprising the support compartment and a second sub-volume comprising a first perfusion compartment, with the second capillary pressure barrier dividing the microfluidic network into the first sub-volume comprising the support compartment and a third sub-volume comprising a second perfusion compartment. Put differently, one capillary pressure barrier defines at least in part the boundary between the at least one support compartment and the at least one perfusion compartment and/or one capillary pressure barrier defines at least in part the boundary between the at least one support compartment and the conduit.

Reservoir

In some examples, the microfluidic network comprises a reservoir or well in fluid communication with a media inlet to the microfluidic channel. The reservoir may be present in a reservoir layer disposed above the cover layer of the microfluidic network. The reservoir may be present to retain a volume of liquid, for example culture media. In a typical embodiment the reservoir is able to retain a larger volume of fluid than is or can be retained by the microfluidic channel. The reservoir may be an adjacent well to the well aligned with the conduit on a bottomless microtitre plate disposed on top of the microfluidic layer and be fluidically connected to the perfusion compartment. The reservoir may be an adjacent well to the well aligned with the conduit on a bottomless microtitre plate disposed on top of the microfluidic layer and be fluidically connected to the support compartment. In other examples, the reservoir may be a well on the same microtitre plate, but spatially distant from the well of the conduit. It will be understood that the proximity of the reservoir to the well of the conduit is not critical to the operation of the device as long as the two are each in fluid communication with the microfluidic layer.

In some examples, the microfluidic network comprises more than one, for example two, or more, reservoirs in fluid communication with the microfluidic layer via an aperture in the cover layer which may be termed an inlet, or an outlet, of the microfluidic layer as appropriate. In the embodiment in which at least two reservoirs are present in the microfluidic network, a first reservoir may be used for introducing a fluid, for example culture media into the microfluidic network, while the second reservoir may function as a vent, or overflow compartment for receiving the fluid during performance of the methods of the present invention.

Enclosure

In some examples, the microfluidic cell culture device comprises an enclosure, that at least partially encloses or covers an exterior part of the base, an exterior part of the cover, or both. In some examples, the enclosure at least partially encloses or covers a reservoir layer, for example a microtitre plate disposed on the cover of the microfluidic network. The enclosure enables the isolation of the environment within the microfluidic network so that the cell culture can be maintained sterile and to exclude dust and other small/ultra-fine particles. In some examples, the enclosure has the form of a plate with a rim extending from the edge thereof. In some examples, the enclosure is configured to engage with an abutting surface of the device so as to form a seal. In some examples, the rim of the enclosure engages with the abutting surface of the device. In some examples, the enclosure is configured to engage with the device in a non-airtight manner. In some examples, the enclosure is configured to engage with the device in a non-airtight manner, but engages with the device so as to provide an arduous or tortuous flow path into the enclosure and/or device.

In some examples, the microfluidic device comprises a first enclosure that at least partially encloses or covers an exterior of the base, and a second enclosure that at least partially encloses or covers an exterior of the cover or a reservoir layer disposed on the cover. In some examples, the enclosure is a single enclosure that completely encloses an exterior of the base and an exterior of the cover or reservoir layer. In some examples, the enclosure is a single enclosure that completely encloses the complete microfluidic device. In some examples, all or part of the enclosure is removable from the device. For the avoidance of doubt, references herein to any particular feature of an or the or the at least one enclosure are to an enclosure covering the base, an enclosure covering the cover, or both enclosures.

In some examples, the enclosure is provided with a port for fluid exchange. In some examples, the enclosure is provided with tubing for guiding the fluid flow. In some examples, the enclosure is provided with a window or transparent portion for optical access. In some examples, the enclosure is provided with a filter for exchanging fluid without contamination. In some examples, the enclosure is provided with a tortuous path for exchanging gaseous fluids without contamination. The tortuous path may be provided between the enclosure and the exterior of the base or cover or reservoir layer when the enclosure is engaged with the microfluidic device. In some examples, the tortuous path is provided within the enclosure itself. Tortuous paths effectively limit flow of bacteria, particulates and other matter that could negatively impact on a cell culture experiment being performed within the microfluidic cell culture device.

In some examples, the enclosure comprises more than one fluidic inlet and more than one fluidic outlet. In some examples, the more than one fluidic inlet and more than one fluidic outlet are connected to the conduits of a plurality of microfluidic networks via connecting channels. In some examples, the number of fluidic inlets is different than the number of outlets and/or the number of connected conduits, thereby allowing the fluidic path to split and/or merge. Such configurations enable the routing of fluid from a single inlet in the device through multiple conduits and/or outlets, or from multiple inlets and/or conduits to a single outlet. In some examples, the enclosure is connected to a positive or negative pressure source as described herein.

Methods

Method of Creating a Fluid-Fluid Interface

In one example there is provided a method of creating a fluid-fluid interface in a microfluidic cell culture device comprising a microfluidic network having a base, a microfluidic channel, and a cover, with at least one perfusion compartment and at least one support compartment inside the microfluidic channel, and the base and cover each comprising an aperture thereby defining a conduit through the microfluidic channel; the method comprising:

- introducing a support scaffold into the at least one support compartment so as to form a scaffold surface facing the conduit;
- introducing a medium containing cells into the conduit via the aperture in the cover while preventing flow of the medium from the conduit via the aperture in the base;
- allowing the cells to form into a layer on the scaffold surface; and
- removing the medium from the conduit to expose the cells.

In some examples, the support scaffold comprises a membrane. In some examples, the support scaffold comprises a gel and introducing the support scaffold into the at least one support compartment comprises introducing a liquid gel-precursor. In some examples, the liquid precursor is pinned in the support compartment so as to form a scaffold surface facing the conduit.

Thus, in one example there is provided a method of creating a fluid-fluid interface in a microfluidic cell culture device comprising a microfluidic network having a base, a microfluidic channel, and a cover, with at least one perfusion compartment and at least one support compartment inside the microfluidic channel, and the base and cover each comprising an aperture thereby defining a conduit through the microfluidic channel; the method comprising:

- introducing a gel or gel-precursor into the at least one support compartment;
- pinning the gel or gel-precursor in the at least one support compartment so as to form a gel surface facing the conduit;
- introducing a medium containing cells into the conduit via the aperture in the cover while preventing flow of the medium from the conduit via the aperture in the base;
- allowing the cells to form into a layer on the gel surface; and
- removing the medium from the conduit to expose the cells.

In some examples, the methods described herein comprise:

- introducing a gel or liquid gel-precursor into the at least one support compartment;
- pinning the gel or liquid gel-precursor in the at least one support compartment and allowing the volume of gel or liquid gel-precursor to cure or gelate so as to form a cured gel surface facing the conduit.

In some examples, the methods described herein may comprise introducing a volume of gel or liquid gel-precursor into the support compartment and allowing the volume of gel or liquid gel-precursor to be confined by a capillary pressure barrier; and allowing the volume of gel or liquid gel-precursor to cure or gelate so as to form a cured gel surface facing the conduit. In some examples, the volume of gel or liquid gel-precursor may be a single droplet or droplet-sized volume of a gel or liquid gel-precursor.

The gel or liquid gel-precursor includes any hydrogel known in the art suitable for cell culture. Hydrogels used for cell culture can be formed from a vast array of natural and synthetic materials, offering a broad spectrum of mechanical and chemical properties. For a review of the materials and methods used for hydrogel synthesis see Lee and Mooney (Chem Rev 2001; 101 (7): 1869-1880). Suitable hydrogels promote cell function when formed from natural materials and are permissive to cell function when formed from synthetic materials. Natural gels for cell culture are typically formed of proteins and ECM components such as collagen, fibrin, hyaluronic acid, or Matrigel, as well as materials derived from other biological sources such as chitosan, alginate or silk fibrils. Since they are derived from natural sources, these gels are inherently biocompatible and bioactive. Permissive synthetic hydrogels can be formed of purely non-natural molecules such as poly(ethylene glycol) (PEG), poly(vinyl alcohol), and poly(2-hydroxy ethyl methacrylate). PEG hydrogels have been shown to maintain the viability of encapsulated cells and allow for ECM deposition as they degrade, demonstrating that synthetic gels can function as 3D cell culture platforms even without integrin-binding ligands. Such inert gels are highly reproducible, allow for facile tuning of mechanical properties, and are simply processed and manufactured.

The gel or gel precursor can be provided to the microfluidic cell culture device, for example to the support compartment of a device as described above. After the gel or gel precursor is provided, it is caused or allowed to gelate, prior to introduction of a further fluid into the perfusion compartment, for example. Suitable (precursor) gels are well known in the art. By way of example, the gel precursor may be a hydrogel, and is typically an extracellular matrix (ECM) gel. The ECM may for example comprise collagen, fibrinogen, fibronectin, and/or basement membrane extracts such as Matrigel or a synthetic gel. The gel precursor may, by way of example, be introduced into the support compartment with a pipette via a well or reservoir in fluid communication with the support compartment.

The gel or gel precursor may comprise a basement membrane extract, human or animal tissue or cell culture-derived extracellular matrices, animal tissue-derived extracellular matrices, synthetic extracellular matrices, hydrogels, collagen, soft agar, egg white and commercially available products such as Matrigel.

Basement membranes, comprising the basal lamina, are thin extracellular matrices which underlie epithelial cells in vivo and are comprised of extracellular matrices, such as proteins and proteoglycans. In one example, the basement membranes are composed of collagen IV, laminin, entactin, heparan sulfide proteoglycans and numerous other minor components (Quaranta et al, Curr. Opin. Cell Biol. 6, 674-681, 1994). These components alone as well as the intact basement membranes are biologically active and promote cell adhesion, migration and, in many cases growth and differentiation. An example of a gel based on basement membranes is termed Matrigel (U.S. Pat. No. 4,829,000). This material is very biologically active in vitro as a substratum for epithelial cells.

Many different suitable gels for use in the method of the invention are commercially available, and include but are not limited to those comprising Matrigel rgf, BME1, BME1rgf, BME2, BME2rgf, BME3 (all Matrigel variants) Collagen I, Collagen IV, mixtures of Collagen I and IV, or mixtures of Collagen I and IV, and Collagen II and III), puramatrix, hydrogels, Cell-Tak™, Collagen I, Collagen IV, Matrigel® Matrix, Fibronectin, Gelatin, Laminin, Osteopontin, Poly-Lysine (PDL, PLL), PDL/LM and PLO/LM, PuraMatrix® or Vitronectin. In one preferred embodiment, the matrix components are obtained as the commercially available Corning® MATRIGEL® Matrix (Corning, NY 14831, USA).

The gel or gel-precursor is introduced into a device described herein and confined by a capillary pressure barrier in the microfluidic device, for example to the support compartment, and then caused or allowed to gelate if required.

In one example, a droplet of a sufficient volume is introduced such that the cured gel is located substantially entirely within the support compartment that is within the microfluidic layer. In one example, the gelled droplet does not block the aperture in the microfluidic cover layer, in which case the unblocked or open region of the aperture can be used as a vent. A vent thus generally comprises an opening or aperture in the cover layer allowing evacuation of air when loading the microfluidic channel through the inlet. In one example, a droplet of a sufficient volume is introduced such that the droplet is confined by a capillary pressure barrier at the boundary between the support compartment and perfusion compartment, and/or by the rim of the aperture in the cover and/or the rim of the aperture in the base which can each also function as capillary pressure barriers.

In some examples, the rim of the base aperture functions as a capillary pressure barrier to prevent flow of medium from the conduit when it is added. In some examples, a removable polymer film may be in contact with the underside of the base layer so as to cover the base aperture while the medium containing cells is introduced into the conduit. It will be understood that it is most convenient to fill the conduit when the microfluidic device is in an "in use" orientation, meaning that the conduit will be most conveniently filled via the cover aperture while flow through the base aperture is prevented. However, it is immediately recognisable to those skilled in the art that it would equally be possible to invert the microfluidic device and fill the conduit via the base aperture while preventing flow through the cover aperture.

The method includes introducing a medium containing cells into the conduit via the aperture in the cover while preventing flow of the medium from the conduit via the aperture in the base. However, it will be apparent that the medium containing cells could as easily be introduced into the conduit via the aperture in the base while preventing flow of the medium from the conduit via the aperture in the cover.

In some examples, at least a portion of the medium is introduced into the conduit separately from the cells, with the cells being added to the at least a portion of the medium separately via the base aperture and/or the cover aperture. Any liquid handling technique could be used to introduce the cells into the conduit, including non-contact dispensing techniques such as acoustic droplet dispensers. In some examples, the conduit is prewetted with a portion of medium, prior to addition of the cells, particularly if small volumes of medium containing the cells are being introduced.

Once the medium containing cells has been added to the conduit, the cells present are allowed to settle onto the surface of the gel lining the conduit. In some examples, the cells are allowed to form into a layer through gravity and/or inclination of the microfluidic device. The degree of inclination may depend on the relative positions of the base aperture and cover aperture and resulting gradient of gel surface between the two. In some examples, the degree of inclination at any one time may be up to 90°, for example up to 80°, for example up to 70°, for example up to 60°, for example up to 50°, for example up to 40°, for example up to 30°, for example about 20° from horizontal.

In some examples, the cells comprise epithelial cells, for example lung epithelial cells, skin epithelial cells, gut epithelial cells, corneal epithelial cells, or mucus producing epithelial cells. In some examples, the cells comprise any epithelial cell found at a fluid-fluid interface in vivo.

Once the cells have become attached to the gel surface, the remaining medium can be carefully removed from the conduit. Removing the medium may be performed cautiously, to avoid dislodging any attached cells. In some examples, the medium is removed from the conduit by one or more of: a pressure pulse; inertia; a change of surface tension in the medium pinned at the aperture in the base; a change of contact angle between the medium and the solid parts of the conduit; aspiration; contacting the medium with a receiving receptacle from above or below the device; mechanical, acoustic, electrostatic, electromagnetic or other actuation; and evaporation. The surface tension in the medium and the contact angle between the medium and the solid parts of the conduit may be changed by addition of a surfactant, for example, or by changing the surface charge of the substrate (electrowetting). Removal of the medium exposes the cells, creating in the first instance an air-air interface, since both the conduit and the perfusion compartment are empty. In some examples the fluid-fluid interface is therefore an air-air interface. In other examples, the fluid-fluid interface is an air-liquid interface, or a liquid-liquid interface, depending on the nature of the experiment and whether the perfusion compartment and/or the conduit are filled with liquid or air/gas.

In some examples, a supply of nutrients is provided to the attached cells via the perfusion compartment(s). For example, the supply of nutrients provided to the cells can be transported from the at least one perfusion channel through the at least one support compartment to the cells via diffusion or interstitial flow through the permeable interface of the support compartment. The permeable interface can be an extracellular matrix pinned by one or more capillary pressure barriers as described herein (including the rim of an aperture) or a permeable membrane which may have an ECM gel within its pores. In some examples, the attached cells are allowed to form on the surface of the support compartment in a manner so as to extend around the entire boundary of the conduit. For example, in the situation in which the conduit has a circular cross-section, the attached cells may be allowed to form a complete tubule encircling the conduit.

In some examples, one or more types of cells are introduced into the perfusion compartment and allowed to form a layer or cell aggregate. In some examples, the one or more types of cells or cell aggregates may be selected from: epithelial or endothelial cells for lining the perfusion compartment, potentially forming a tube or blood vessel; epithelial or endothelial cells to be situated inside a gel, extracellular matrix or scaffold, preferably forming lumened structures, more preferably forming a vascular bed; stromal cells in or on a gel, extracellular matrix or scaffold; muscle cells in or on a gel, extracellular matrix or scaffold; or any other type of cell that may be required to create a desired in vitro model system.

Using capillary pressure barriers enables the formation of stable confined volumes of gel, for example, in the support compartment of the microfluidic network so that addition of a second fluid into the perfusion compartment can take place without displacing the gel or its contents. The device of the present invention is thus configured for spatially controlled co-culture with other cells as described above, and provides means to control the composition of the surrounding medium. Within the methods described, a fluid loaded into a reservoir (herein also referred to as a well) is any of cell culture media, test solutions, buffers, further hydrogels and the like and may optionally comprise cells or cellular aggregates.

By controlling the composition(s) introduced in the reservoir(s) the cell culture device of the present invention enables different modes of cell culture. For example, the composition of fluids introduced into the reservoirs or wells can be changed. Such exchange can be a gradient exchange by introducing a new composition in one of the reservoirs and simultaneously removing the fluid from another reservoir within the same microfluidic network till complete exchange has occurred. Such exchange can be discrete, by aspirating fluid from the reservoir and filling it with the new composition. The fluid volume in the reservoir is much larger than the fluid volume in the microfluidic channel and the levelling between reservoirs occurs almost instantaneously, thereby assuring flushing the microfluidic network with the new fluid without the need for emptying the microfluidic channel network during the procedure.

Method of Investigating a Cellular Response to a Stimulant

In one example, a method of investigating a cellular response to a stimulant comprises creating a fluid-fluid interface in a microfluidic device according to the methods described herein and subjecting the exposed cells to a fluid stream by directing the fluid stream through the conduit.

In one example, a method of investigating a cellular response to a stimulant comprises using an assay plate as described herein and subjecting the exposed cells to a fluid stream by directing the fluid stream through the conduit.

Once the fluid-fluid interface has been created as described above, it becomes possible to perform experiments on the cultured cells to investigate their response to stimulants. For example, a fluid stream directed through the conduit with cellular tubule may include one or more of: air, smoke; a vapour; an aerosol; a pathogen; ultrafine particles; analytes; a candidate pharmaceutical drug; or other compounds of interest. The fluid stream may be a gaseous stream or a liquid stream. Typically, if a lung model has been created and is being investigated, then the fluid stream would usually be a gaseous stream as the interface would be an air-liquid interface to recreate the lung environment.

In some examples, the fluid stream directed through the conduit may not carry a stimulant but instead collects cellular samples from the layer of cells, or induces a shear stress in the layer of cells. In other words, the fluid stream may also serve the purpose of sample collection as well as sample investigation. In some examples, the fluid stream directed through the conduit is merely a culture media to directly provide the cells with nutrients, rather than transporting the nutrients from the perfusion compartment via the support compartment to the cells.

In some examples, an experiment may include subjecting the cells to a stimulant in a first fluid stream, and then collecting the cells using a second fluid stream different to the first fluid stream for the purpose of determining the effect of the stimulant on the cells. In some examples, the cellular response to the stimulant can be monitored in situ, without removing the cells from the conduit. In some examples, determining a cellular response may include assaying one or more of cellular phenotype; cellular morphology and cellular function, depending on the nature of the investigation.

In some examples, the fluid stream directed through the conduit may be at least partially collected, and at least partially recirculated through the conduit a second time, or a plurality of times. The recirculation may be achieved through the use of a pump.

In some examples, the methods include providing a supply of nutrients to the cells via the at least one perfusion compartment, as described previously in connection with the method of forming the fluid-fluid interface. For example, the supply of nutrients may be provided to the cells from the at least one perfusion channel through the at least one support compartment via diffusion or interstitial flow through the permeable interface of the support compartment.

In some examples, the methods include introducing one or more types of cells into the at least one perfusion compartment and allowing the one or more types of cells to form a layer or cell aggregate, optionally before or after the exposed cells are subjected to the fluid stream.

Assay Plate

A further aspect of the present invention provides an assay plate, comprising any of the devices described herein.

In one example there is provided an assay plate, comprising a microfluidic device as described herein with a scaffold or other support structure within the support compartment. In some examples, the microfluidic network of the assay plate comprises one or more cells or cell aggregates, present for example in or on the scaffold or support structure facing the conduit, and/or in a microfluidic channel. In some examples, the scaffold or support structure comprises a gel, an extracellular matrix and/or a membrane. In some examples, the cells or cell aggregates at least partly line the conduit. In some examples, the cells are epithelial cells, for example lung epithelial cells. In some examples, the cells or cell aggregates at least partly line the conduit and thereby form a fluid-fluid interface that can be investigated as described herein.

The assay plate may comprise one or more cells or cell aggregates which have been cultured by the methods described herein. The dimensions of the assay plate may be consistent or compatible with the standard ANSI/SLAS microtitre plate format. In particular, the dimensions of the footprint or circumference of the assay plate may be consistent with the ANSI/SLAS standard for microtiter plates.

Also described are assay plates, or cell culture devices produced by any of the methods described herein.

Kits

The present disclosure also provides kits and articles of manufacture for using the microfluidic devices and assay plates described herein. In some examples, the kit may comprise the device or assay plate described herein and one or more of: a gel, gel-precursor composition or other extracellular matrix composition; one or more cells or cell types; growth media; and one or more reagent compositions.

The kit may further comprise a packaging material, and a label or package insert contained within the packaging material providing instructions for use.

The kits may further include accessory components such as a second container comprising suitable media for introducing the cells, and instructions on using the media.

DETAILED DESCRIPTION OF FIGURES

The present invention will now be described by way of example only with reference to the drawings.

Figure 2:
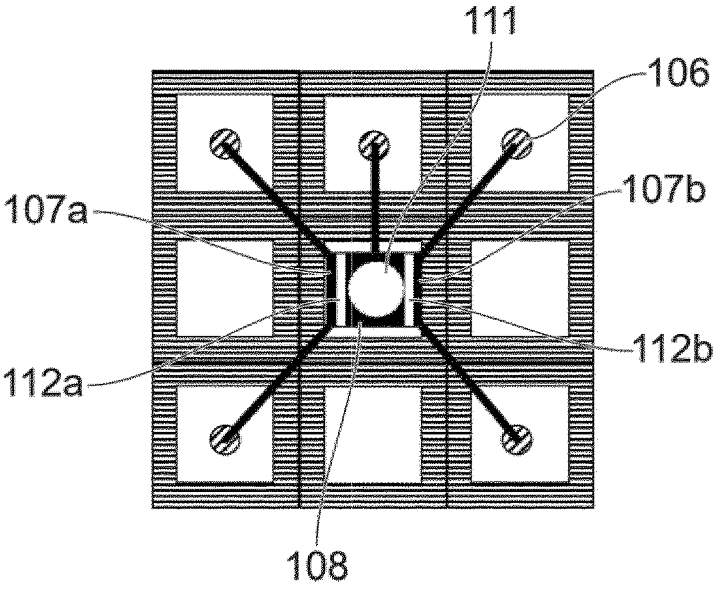
FIG. 2 shows a horizontal top view of the microfluidic network of FIG. 1.
Figure 3:
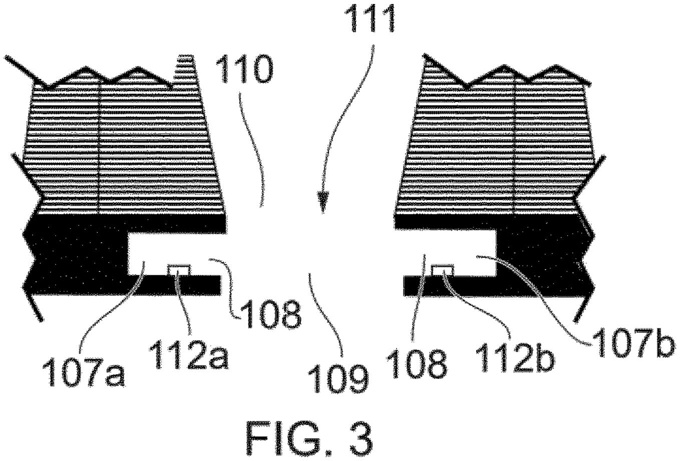
FIG. 3 shows a close up vertical cross-section of the microfluidic network of FIG. 1.

A first example of a microfluidic device is schematically shown in FIGS. 1 to 3. The device 100 as shown in FIG. 1 generally comprises a base 101, a microfluidic channel 102 in a microfluidic layer and a cover 103 (all shown in solid). A top layer 104 in the form of a multiwell bottomless plate is disposed on top of the cover layer and includes a well or reservoir 105. Media inlets 106 are present in the cover layer of the microfluidic layer. Two capillary pressure barriers 112*a* and 112*b* are present on the base 101 of the device and accessible via aperture 109 in the base and aperture 110 in the cover layer 103. In this example, one well or reservoir 105 is positioned above base aperture 109 and cover aperture 110. Separate wells are provided above media inlets 106. A conduit 111 is provided through the microfluidic device, defined by base aperture 109 and cover aperture 110.

As can be seen in FIG. 2 and FIG. 3, microfluidic channel 102 is divided by capillary pressure barriers 112*a* and 112*b* into three sub-volumes. On the left of capillary pressure barrier 112*a* is a first perfusion compartment 107*a*, with flow channels leading to its dedicated media inlet and outlet. A corresponding second perfusion compartment 107*b* can be found to the right of capillary pressure barrier 112*b*. The region of microfluidic channel 102 within first and second capillary pressure barriers 112*a* and 112*b* defines support compartment 108, which in this example encircles base aperture 109 and cover aperture 110 and the thereby defined conduit 111. Support compartment 108 also has its own media inlet connected by a dedicated flow channel. In this example, a dedicated media outlet for support compartment 108 is not required, as conduit 111 serves as a vent when material is introduced into support compartment 108.

Base aperture 109 and cover aperture 110 in FIG. 2 as well in subsequent figures are depicted as circular shaped apertures. However, it will be understood that the aperture can have any shape, with circular and square being preferred.

FIGS. 4A to 4D show further examples of microfluidic cell culture devices with differing configurations with regard to capillary pressure barrier placement and aperture dimensions.

Figure 4A:
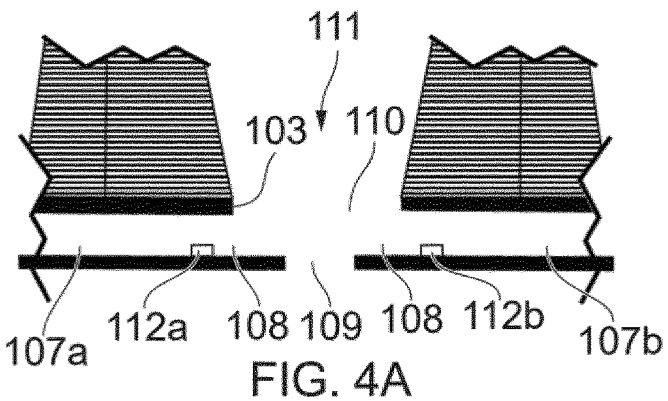
FIGS. 4A to 4D show vertical cross-sections views of exemplary configurations for a microfluidic network as used in a device as herein described.

FIG. 4A shows an example device in which base aperture 109 is much narrower than cover aperture 110. Consequently, when support compartment 108 is filled with gel, the gel surface which faces cover aperture 110 will slope down toward base aperture 109. Put another way, conduit 111 being defined by apertures 109 and 110, a surface of a gel within support compartment 108 and the reservoir above will have a frusto-conical cross section, tapering toward base aperture 109. In the device of FIG. 4A, capillary pressure barriers 112*a* and 112*b* are arranged on base 101, projecting into the microfluidic channel. Reducing the base aperture width as in this Figure has the effect of reducing the (chance of) leakage through the base aperture, i.e. reducing the pull of gravity. A wider cover aperture has the advantage of improved access to the conduit.

Figure 4B:
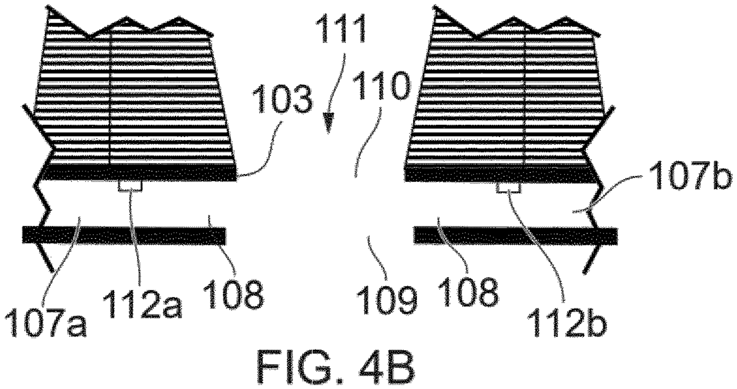

FIG. 4B shows an example device in which base aperture 109 is much wider than cover aperture 110. Consequently, when support compartment 108 is filled with gel, the gel surface which faces cover aperture 110 will extend out toward base aperture 109. Put another way, conduit 111 being defined by apertures 109 and 110, a surface of a gel within support compartment 108 and the reservoir above will have an hour-glass type cross section. In the device of FIG. 4B, capillary pressure barriers 112*a* and 112*b* are arranged on cover 103, projecting into the microfluidic channel. A wider base aperture such as is shown in this Figure allows for easier access from the bottom of the device, for example when seeding cells through the bottom aperture or when extracting single or multiple cells from the conduit. Furthermore, having a wider base aperture may improve imaging quality when there is no bottom substrate between the cells and the imaging apparatus.

Figure 4C:
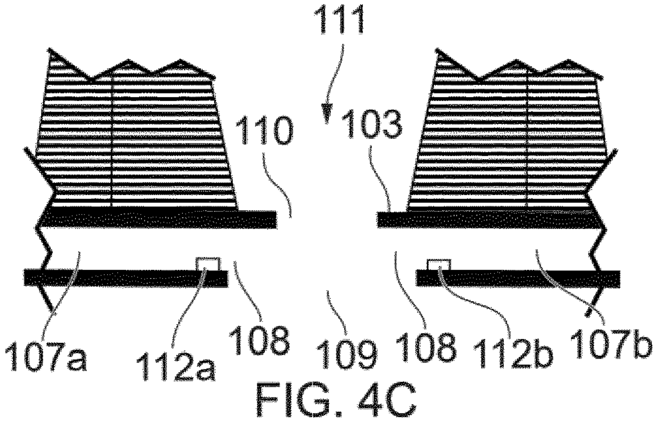
Figure 4D:
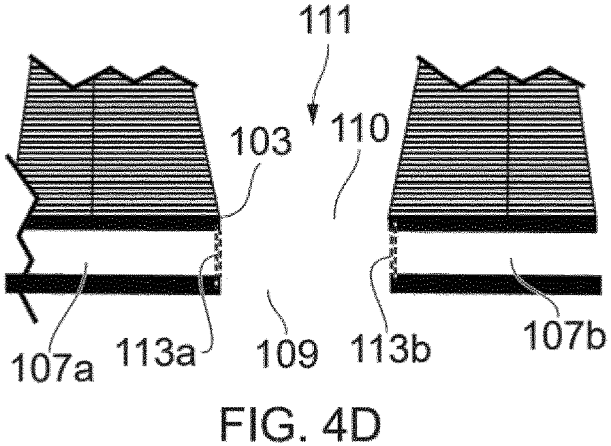

FIG. 4C shows an example device in which base aperture 109 is much narrower than cover aperture 110. Consequently, when support compartment 108 is filled with gel, the gel surface which faces cover aperture 110 will slope down toward base aperture 109. Put another way, conduit 111 being defined by apertures 109 and 110, a surface of a gel within support compartment 108 and the reservoir above will have a frusto-conical cross section, tapering toward cover aperture 110. In the device of FIG. 4C, capillary pressure barriers 112*a* and 112*b* are arranged on base 101, projecting into the microfluidic channel but much closer to base aperture 109 than in the example of FIG. 4A. Having a base aperture much wider than the cover aperture as in the lay-out of FIG. 4C allows for a cell layer orientation that is reversed from the cell layer orientation in FIG. 5. This could be beneficial for having different fluid flow patterns around the cell layer or for having the same fluid flow along the cell layer when the fluid flow comes from below through the base aperture.

FIGS. 5A to 5G depict the steps of a method of creating a fluid-fluid interface in a microfluidic device as described herein.

Figure 5A:
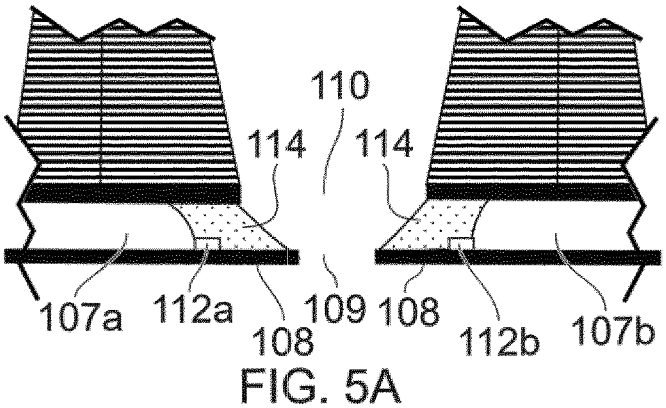
FIGS. 5A to 5G show a schematic representation of the steps in a method as herein described.

FIG. 5A shows a gel or gel-precursor 114 filled into support compartment 108, pinned in place by base aperture 109, cover aperture 110, and first and second capillary pressure barriers 112*a* and 112*b*.

Figure 5B:
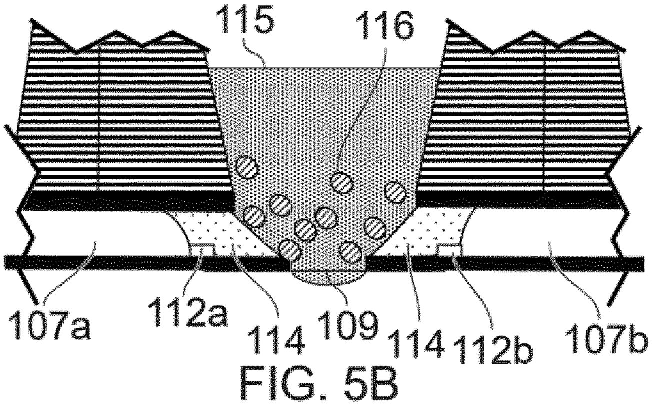

FIG. 5B shows a medium 115 introduced into conduit 111 (not numbered). Cells 116 suspended within medium 115 are shown as beginning to settle toward the lower levels of medium 115. Base aperture 109 is shown functioning as a capillary pressure barrier, pinning medium 115 in place in conduit 111 and preventing it from flowing out.

Figure 5C:
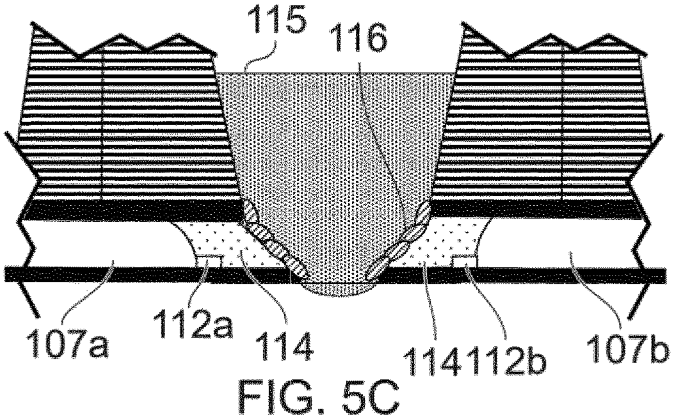
Figure 5D:
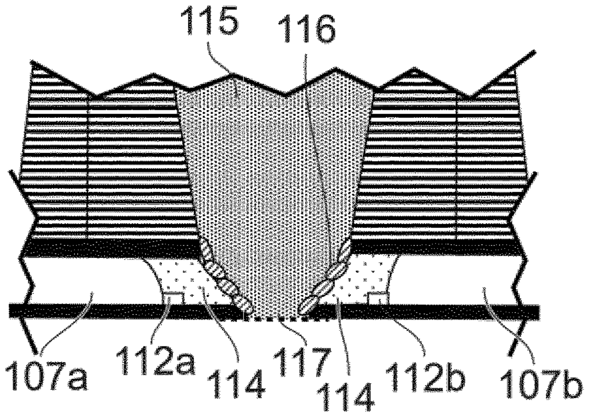

FIG. 5C shows cells 116 forming a layer on the surface of gel 114 facing conduit 111, with medium 116 still pinned by base aperture 109. FIG. 5D shows an alternative set up, in which sacrificial, i.e. temporary film 117 was placed over base aperture 109 to prevent flow of medium 115 through base aperture.

Figure 5E:
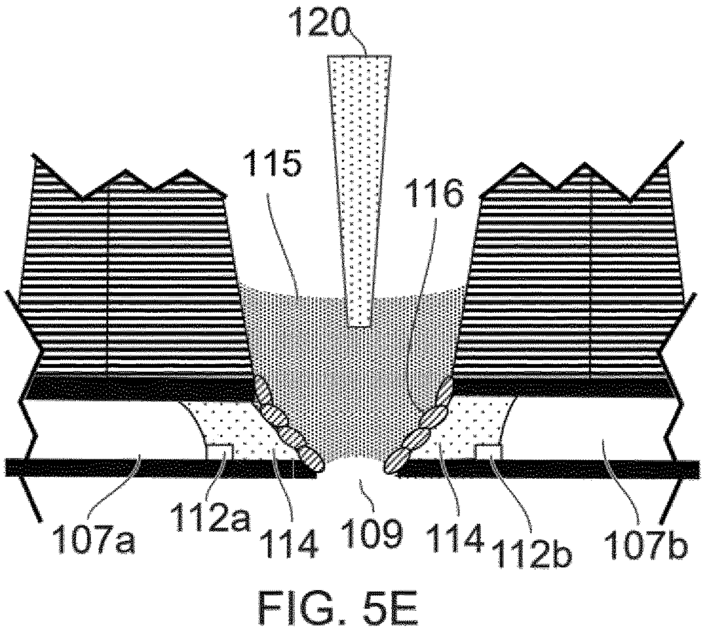
Figure 5F:
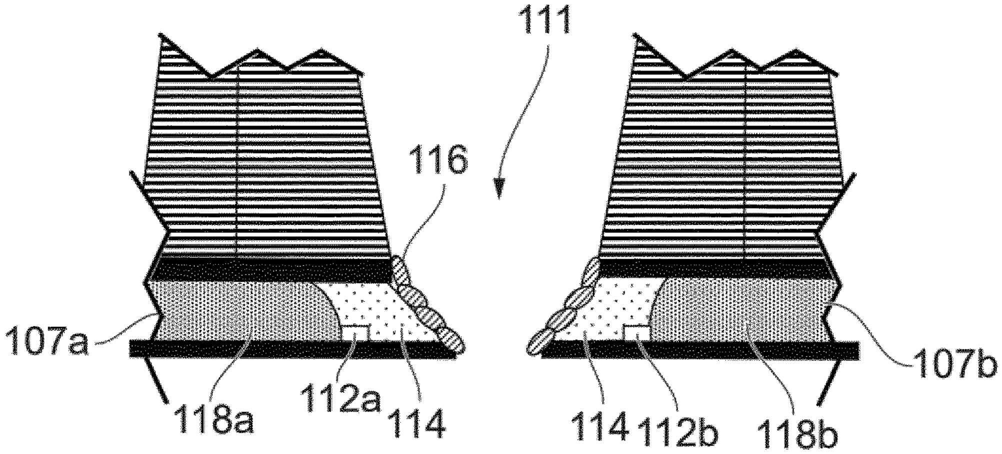

FIG. 5E shows medium 115 being removed from conduit 111 by aspirator 120. Careful removal of medium 115 results in withdrawal of the meniscus of medium 115 from base aperture 109, and in cells 116 being exposed to air, as shown in FIG. 5F. FIG. 5F also shows a second medium 118 introduced into perfusion compartments 107*a* and 107*b*. Second medium 118 may be a cell culture media to provide nutrients to cells 116 via transport through gel 114 in support compartment 108.

Figure 5G:
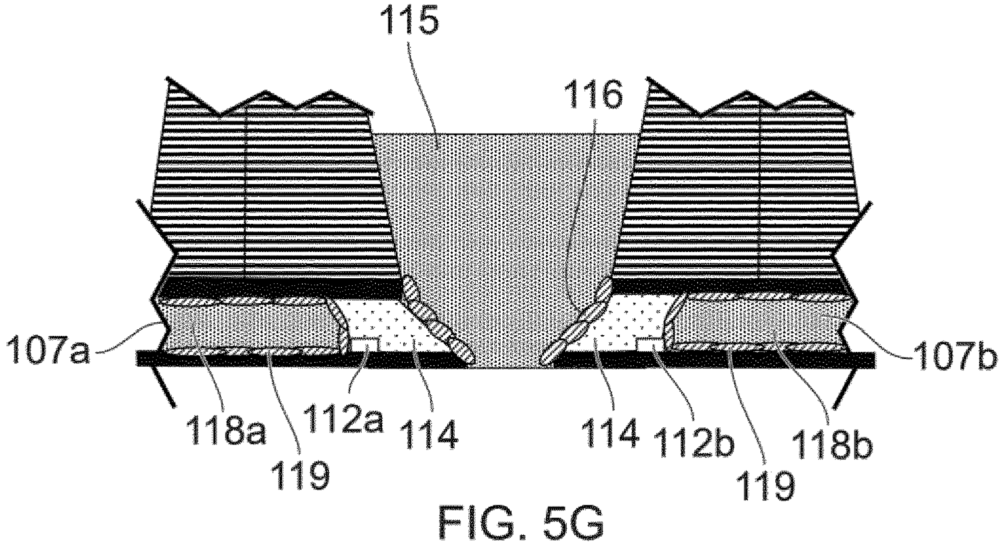

FIG. 5G shows medium 118*a* in perfusion compartment 107*a* and medium 118*b* in perfusion compartment 107*b*. In this example, medium 118*a/b* also includes cells 119, which have formed a lumened structure within their respective perfusion compartments.

Figure 6A:
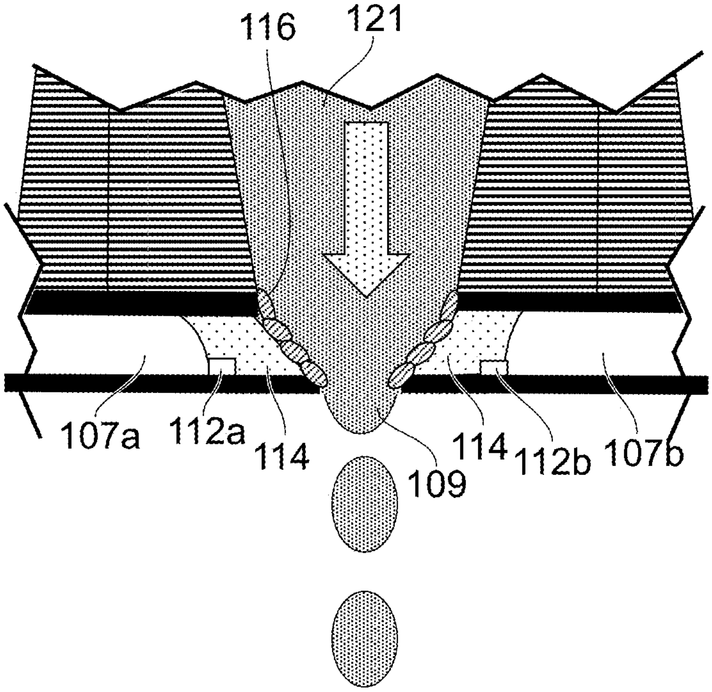
FIGS. 6A, 6B and 7 show schematic representations of an alternative method as herein described.
Figure 6B:
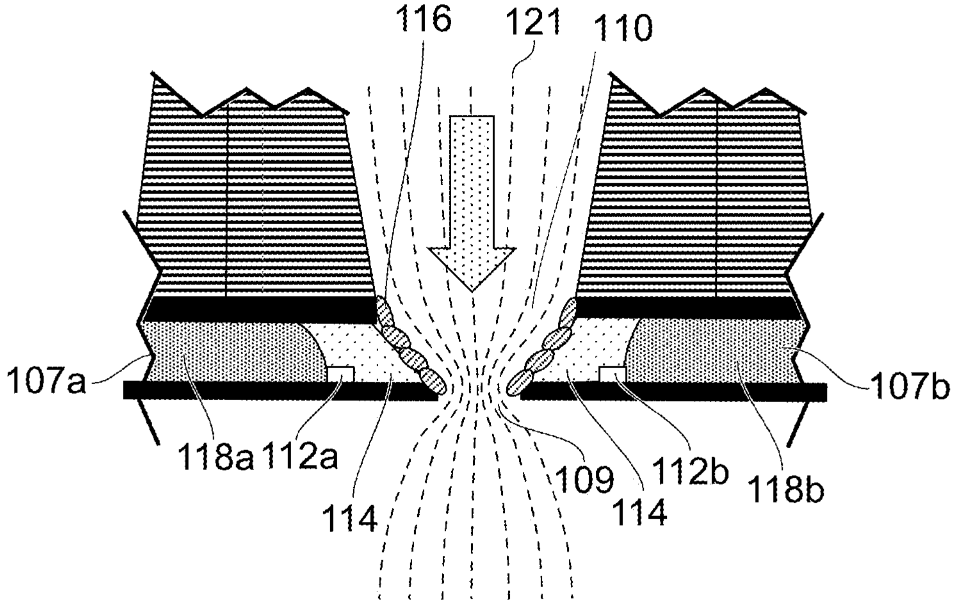
Figure 7:
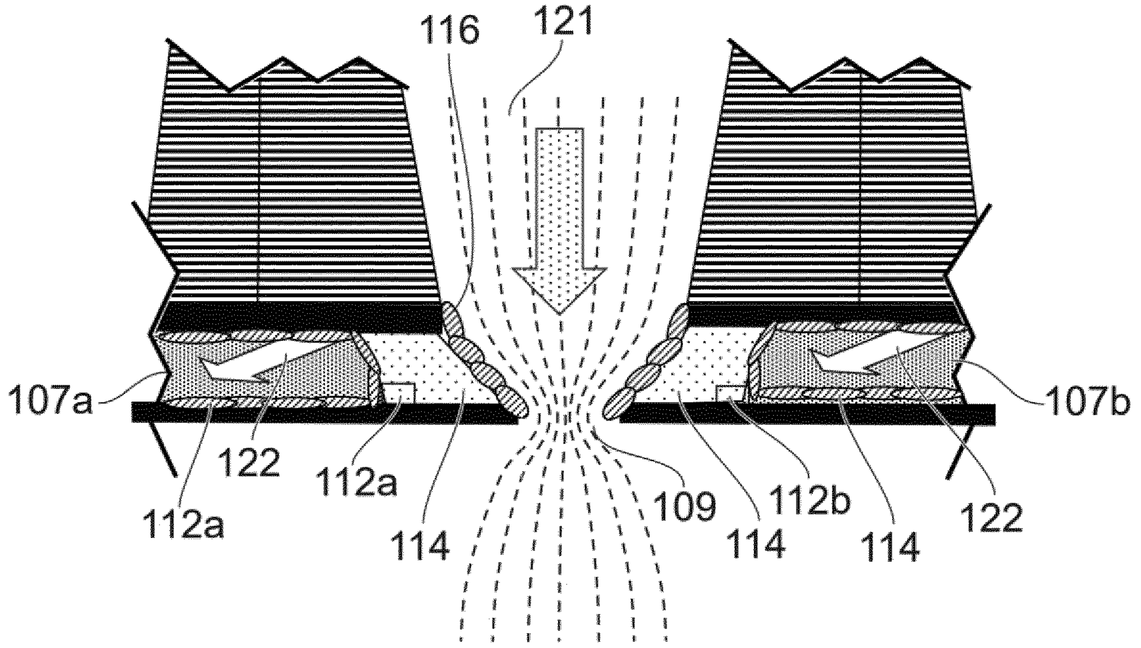

FIGS. 6A, 6B and 7 show methods of investigating the response of cells at a fluid-fluid interface set up as in the methods of FIGS. 5A to 5G. In FIG. 6A, fluid 121 is in the form of a liquid and is being directed through the conduit so as to subject cells 116 to the fluid and its contents. In FIG. 6B, fluid 121 is a gas stream being directed through the conduit. Fluid 121, whether a liquid or gas may contain a stimulant to which cells 116 are to be exposed, with the aim of investigating the cellular response to the stimulant. FIG. 7 shows fluid 121 being directed through the conduit, as in FIG. 6B. In FIG. 7, perfusion compartments 107*a* and 107*b* are lined with a cell layer, for example an epithelial or endothelial lumen, with a second fluid flow through the perfusion compartments and lumened components. The devices described herein therefore enable flow of two different fluids through separate channels, at different flow rates and different compositions as may be required. Thus, flow of media through perfusion compartments 107*a* and 107*b* enables culture of cells 116 for the duration of the investigations into the cellular responses to whatever stimulant is included in fluid 121. While these Figures show the direction of flow of fluid 121 as being in a downward direction, that is entering the device via cover aperture 110 and exiting through base aperture 109, it will be understood that it is also possible to reverse the flow direction and achieve the same results, if desired.

Figure 8:
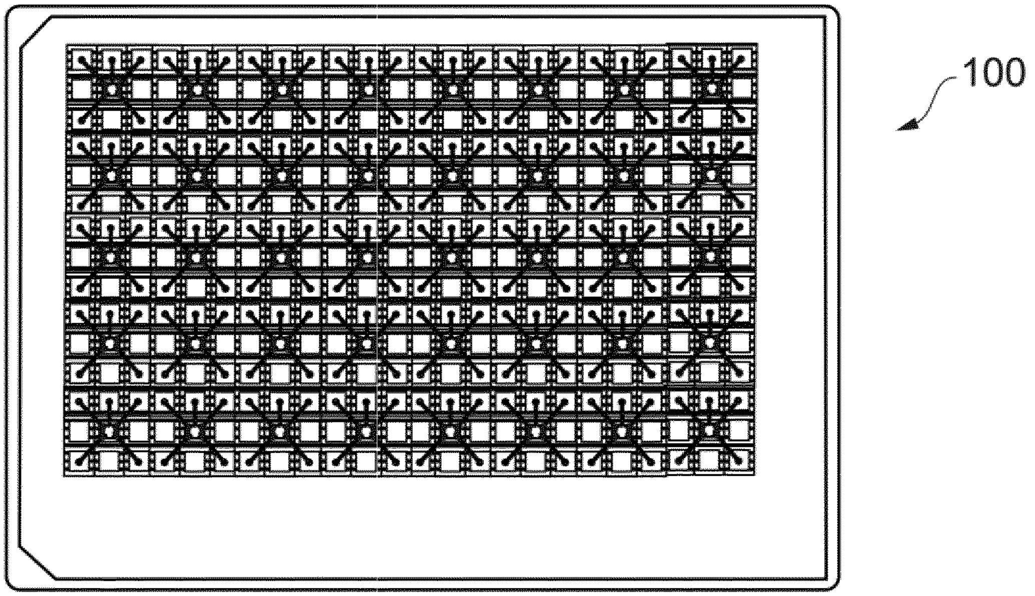
FIG. 8 shows a plan view of a device as described herein consisting of a multi-well configuration of microfluidic networks as herein described.
Figure 9:
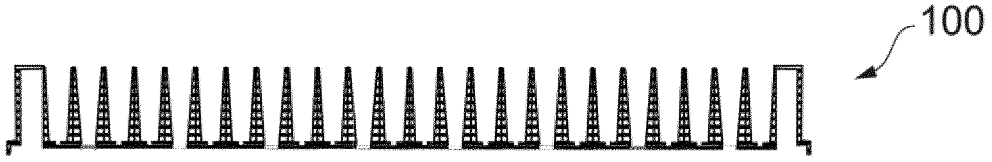
FIG. 9 show vertical cross-section views of devices as herein described and consisting of a multi-well configuration of the microfluidic networks.
Figure 15:
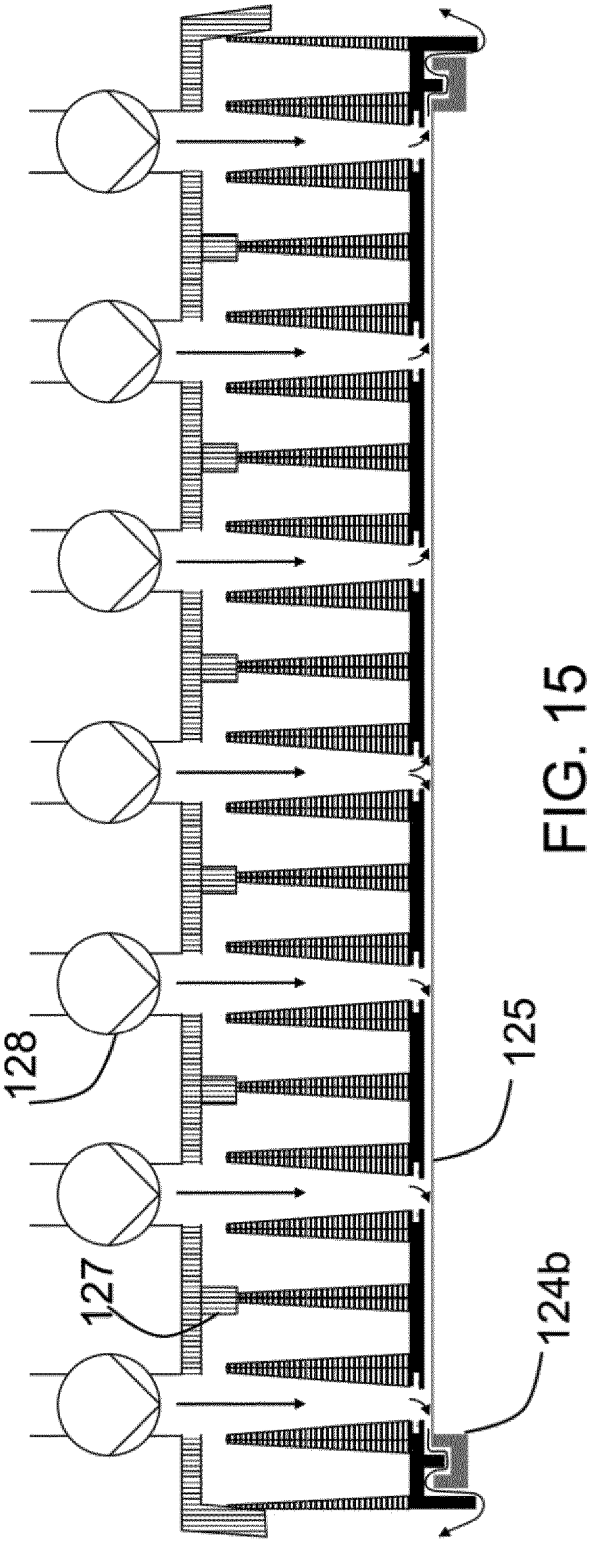
FIG. 15 shows an example microfluidic device with dedicated fluid inlets.

FIG. 8 shows a plan view of a microfluidic device (100) comprising a multi-well configuration of a plurality of the microfluidic networks as herein described. As described, the device is preferably compatible with or based on a microtiter plate footprint as defined by ANSI/SLAS dimensions, as shown in FIG. 15, which shows a bottom view of such a plate comprising 40 separate microfluidic networks such as for example described in FIG. 1. In the centre of each microfluidic network a conduit 111 is indicated. FIG. 9 shows a cross-section of the multi-well configuration of FIG. 8, with conduit extending through the cover and base apertures in each microfluidic network.

Figure 10:
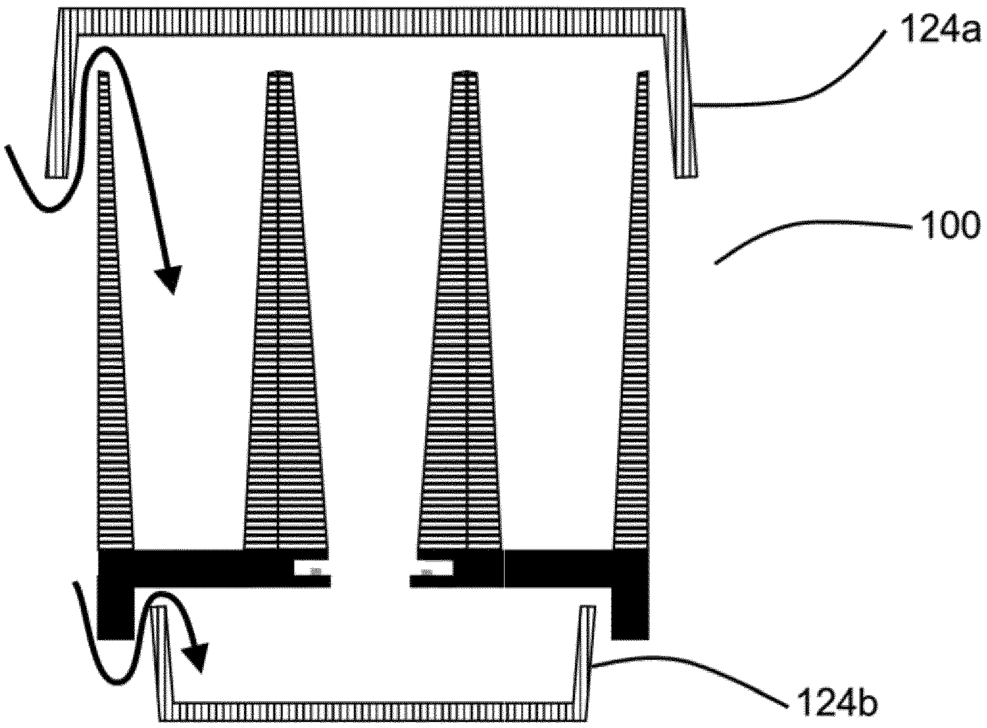
FIG. 10 shows an example microfluidic device with upper and lower enclosures.

FIG. 10 shows a microfluidic device 100 as described herein, provided with enclosures 124*a* and 124*b*. Enclosure 124*a* is provided on a top side of device 100, and rests on top of a reservoir layer (not numbered) of device 100. Enclosure 124*b* is provided on a bottom side of device 100, and sits within two abutments at the outer edges of the base. In each case, enclosures 124*a* and 124*b* do not form a completely airtight seal with device 100, but instead provide tortuous flow paths into device 100 by virtue of extending rims on each enclosure. Tortuous paths, as indicated by the arrows, enable the ingress of particulates, including bacteria, into the device to be prevented, or at least minimised.

Figure 11:
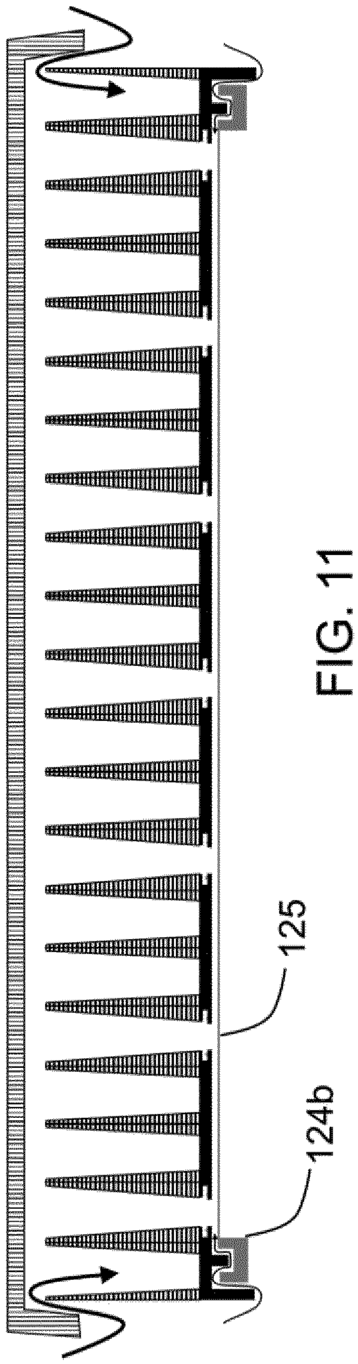
FIG. 11 shows an example microfluidic device with upper and lower enclosures.

FIG. 11 shows another example of a microfluidic device provided with enclosures. In this example, lower enclosure 124*b* is provided with a transparent surface in the form of window 125 to allow optical access to one or more of the individual microfluidic networks. In this example, visual monitoring of experiments being performed in individual microfluidic networks is facilitated by use of window 125.

Figure 12A:
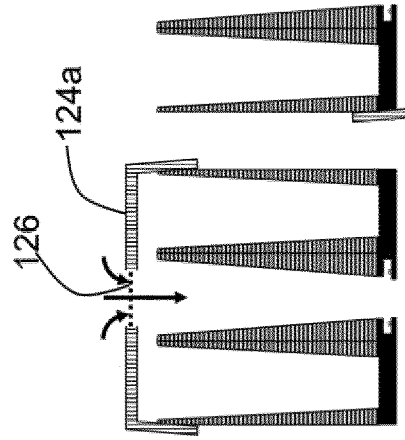
FIGS. 12A to 12D show example microfluidic devices with enclosures including filters.
Figure 12B:
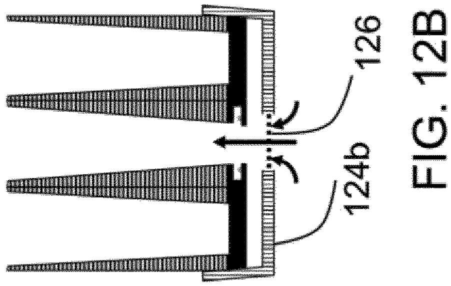
Figure 12C:
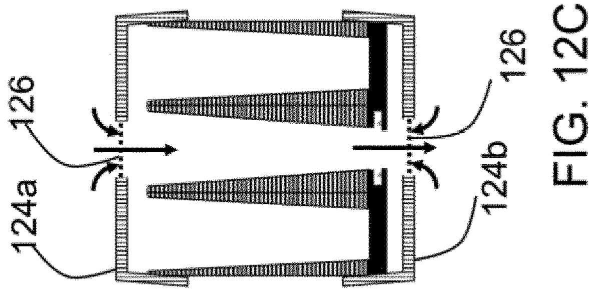
Figure 12D:
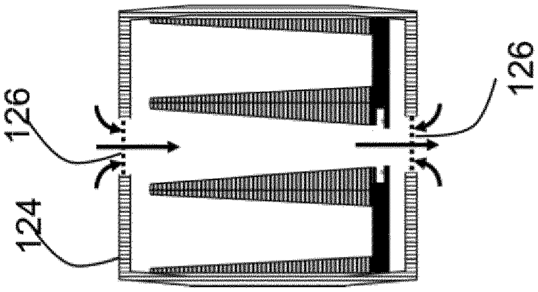

FIGS. 12A to 12D illustrate different examples of microfluidic devices having enclosures as described. In FIG. 12A, upper enclosure 124*a* is provided with filter 126, whereas in FIG. 12B it is lower enclosure 124*b* which is provided with filter 126. In FIG. 12C, the microfluidic device is provided with upper and lower enclosures 124*a* and 124*b*, both provided with filters 126, while in FIG. 12D, a unitary enclosure 124 is provided that completely encloses the microfluidic device and which is provided with filters 126 on upper and lower surfaces. The use of filters, which may be in the form of (permselective) membranes, adsorption columns such as carbon filters, water locks, geometric trapping structures or valves, allows for the selective passage of fluids into or out of the microfluidic device. For example, filters 126 may be selected or configured to exclude organisms, viruses, pathogens, particles, water, or ambient moisture, from entering into the microfluidic device while permitting gas exchange and/or pressure equilibration.

Figure 13:
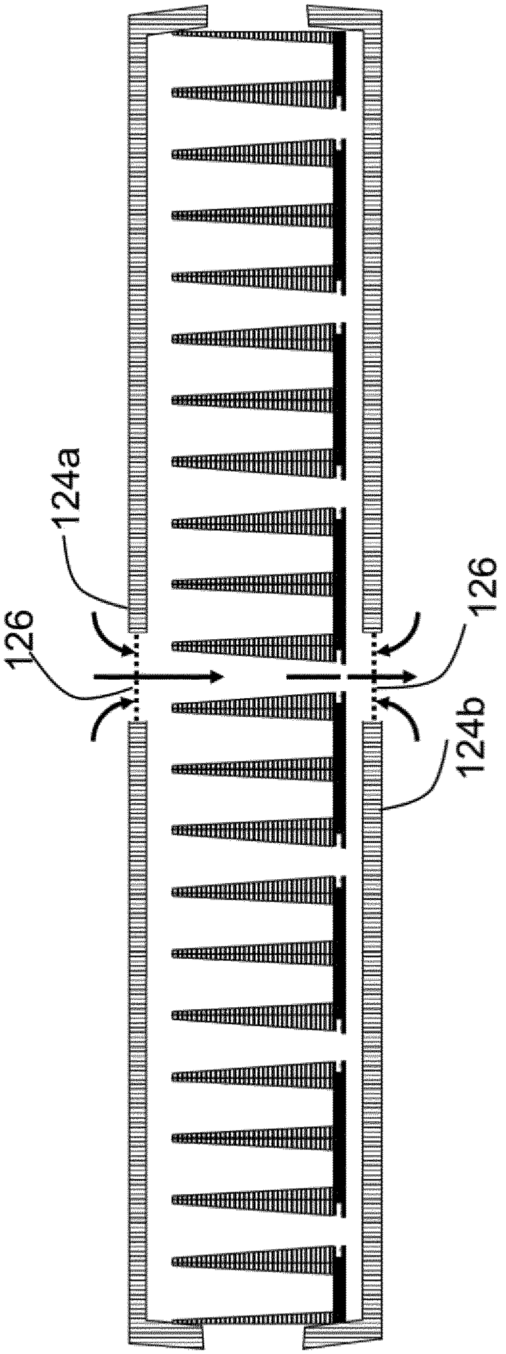
FIGS. 13 and 14 show airflow though example microfluidic devices with enclosures.
Figure 14:
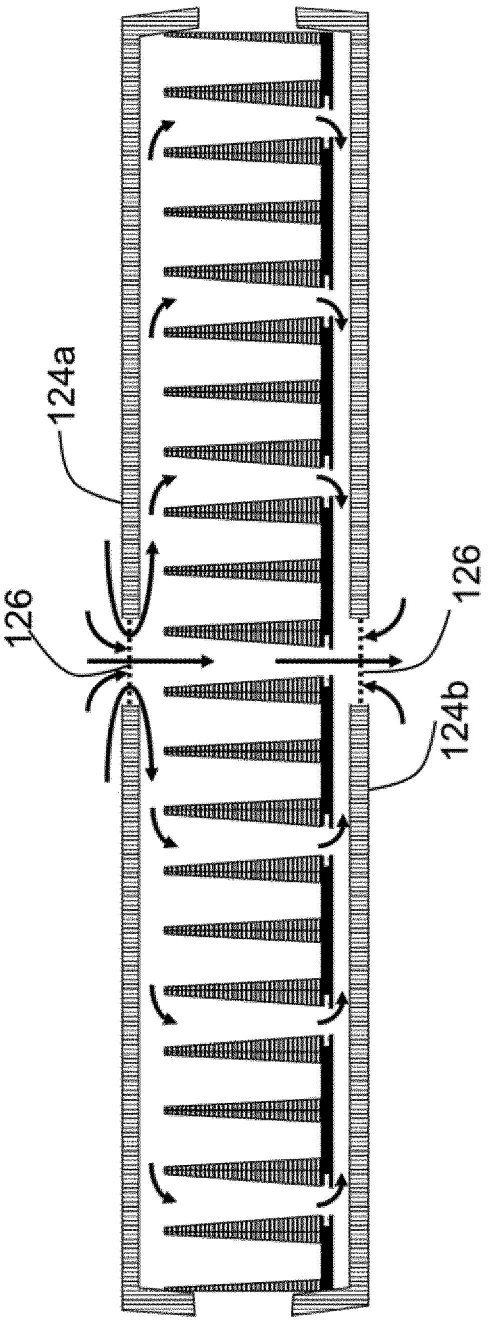

FIG. 13 and FIG. 14 illustrate fluid flow, for example flow of a gaseous stream through the enclosure(s) and microfluidic device. In FIG. 13, filter 126 in upper enclosure 124*a* permits only certain fluids to pass through into the device, with those fluids then passing through a single conduit of a single microfluidic network, and out of lower enclosure 124*b* via a second filter 126. However, in this example device, since all microfluidic networks are in communication with each other, the fluid flow will be more accurately represented by that shown in FIG. 14, rather than the simplified flow shown in FIG. 13. In FIG. 14, fluid entering the microfluidic device via filter 126 in upper enclosure 124*a* is shown as passing through the conduits of each depicted microfluidic network, before combining in the void between the base of the microfluidic network and the lower enclosure 124*b* and exiting through filter 126 in lower enclosure 124*b*. Thus, a fluid stream introduced via a single fluid inlet into the microfluidic device can reach all individual microfluidic networks, enabling high throughput screening of the effect of single test compound, for example, on multiple cellular samples in individual conduits.

In contrast, the example device of FIG. 15 illustrates each microfluidic network having its own, dedicated, fluid inlet to the conduit. Specifically, the upper enclosure is provided with sealing members 127, that engage with the reservoir layer so as to isolate conduits of individual microfluidic networks from each other. Individual or dedicated fluid inlets 128 thus provide fluid solely to a cellular sample in the respective microfluidic network. In the example, dedicated inlets 128 are equipped with a pump to control fluid flow and allow for automation. Fluid streams exiting conduits via base apertures combine in the void between the base and lower enclosure 124*b*, and exit the device via tortuous paths as indicated. In this example, lower enclosure 124*b* is further provided with window 125 to provide optical access to the underside of the microfluidic device. Such a device enables high throughput screening of multiple test compounds on cellular samples, with waste streams being efficiently combined and removed as a single fluid outlet for, for example a waste stream.

Figure 16:
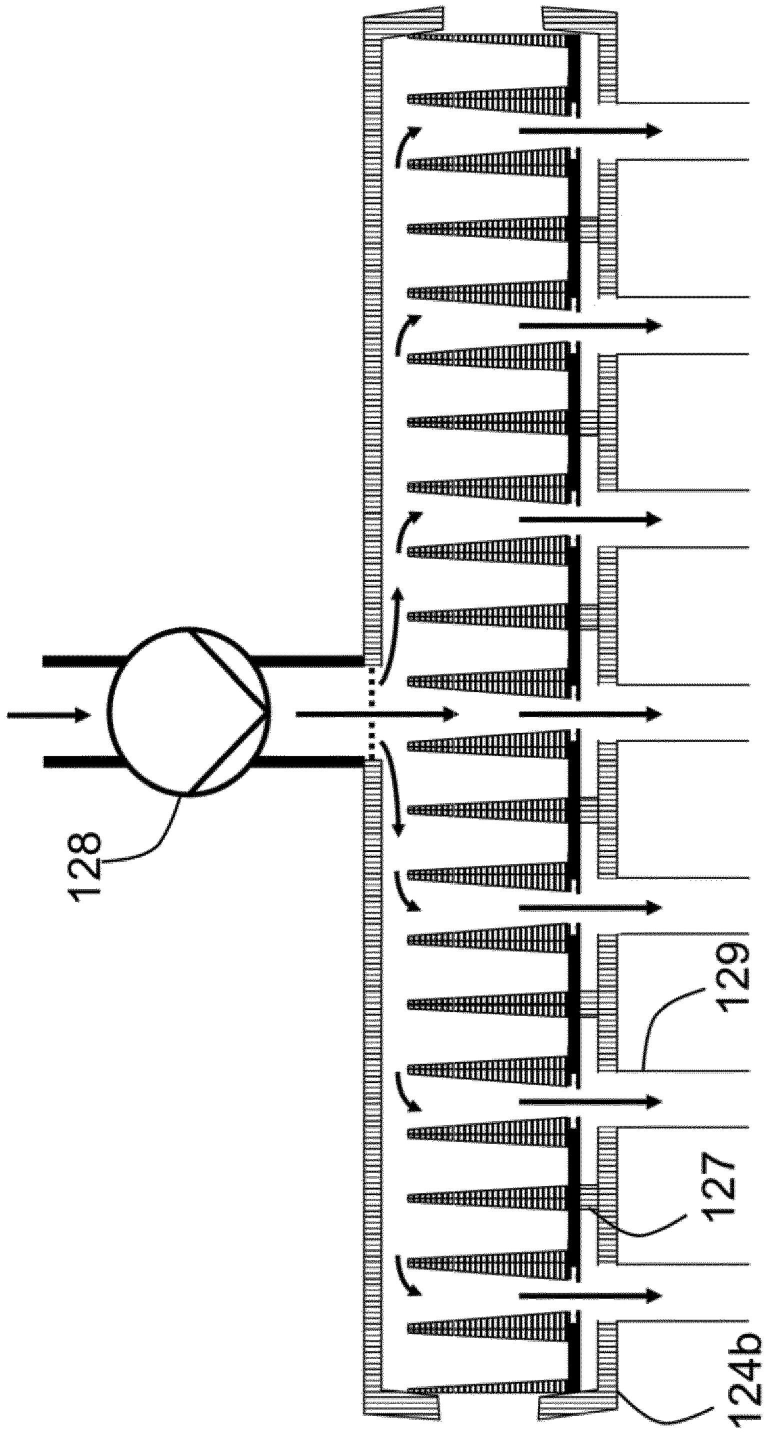
FIG. 16 shows an example microfluidic device with dedicated fluid outlets.

FIG. 16 illustrates another configuration of device for high throughput screening. In this device, a single fluid inlet 128 controls flow of a fluid stream through a filter into the common space above the reservoir layer of the device. The fluid stream can thus pass through the conduit of all microfluidic networks, in a manner similar to that shown in FIG. 14. In contrast to the device of FIG. 14, the device of FIG. 16 is provided with sealing members 127 on lower enclosure 124*b*, and each conduit has its own dedicated fluid outlet 129. Thus, separate cellular samples within the different microfluidic networks can be exposed to a common test fluid, with the exiting fluid streams being prevented from cross-contaminating each other.

Figure 17:
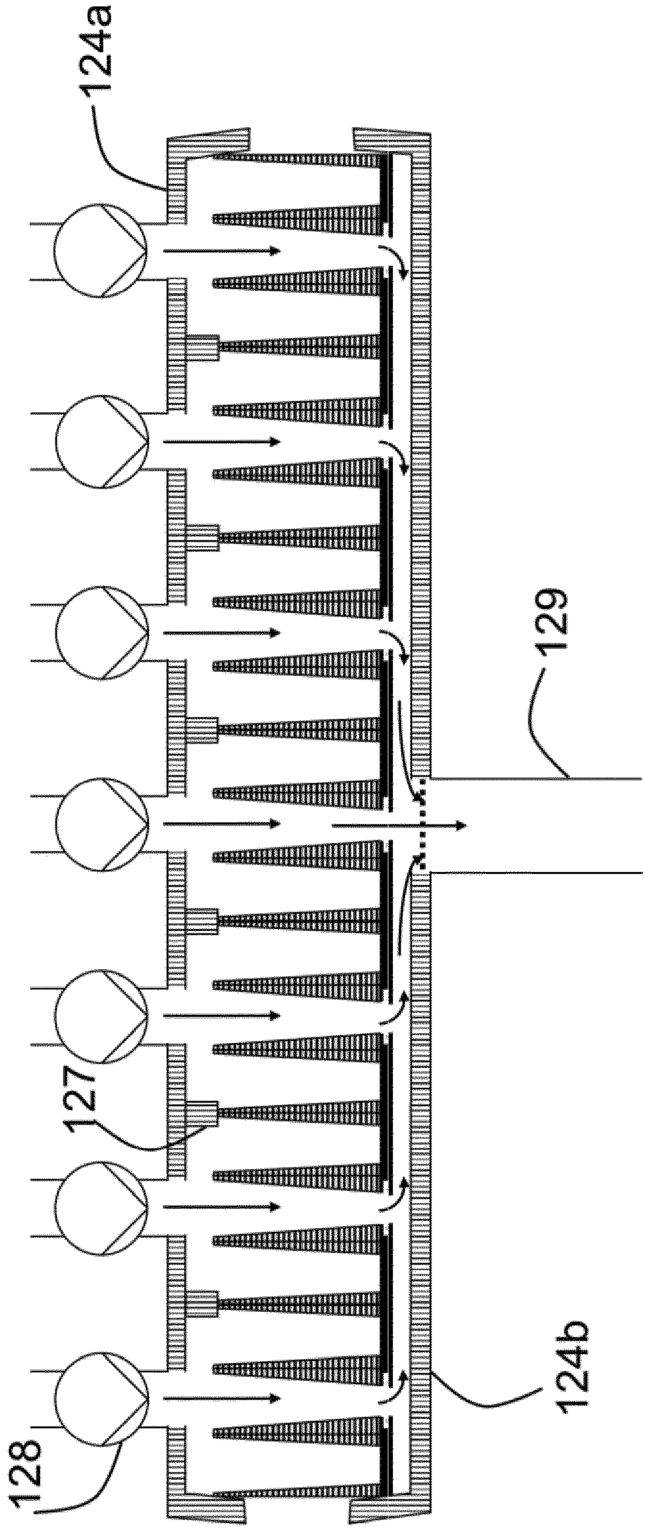
FIG. 17 shows an example microfluidic device with dedicated fluid inlets and a common outlet.

FIG. 17 shows an example microfluidic device similar to that of FIG. 15, with the exception that there is no tortuous path provided at the extremes of the device, with enclosures 124*a* and 124*b* forming airtight seals with the reservoir layer and base of the device. Sealing members 127 allow for individual fluid streams to be introduced to each conduit via dedicated fluid inlets 128, with fluid streams exiting the individual conduits combining and exiting via common fluid outlet 129.

Figure 18:
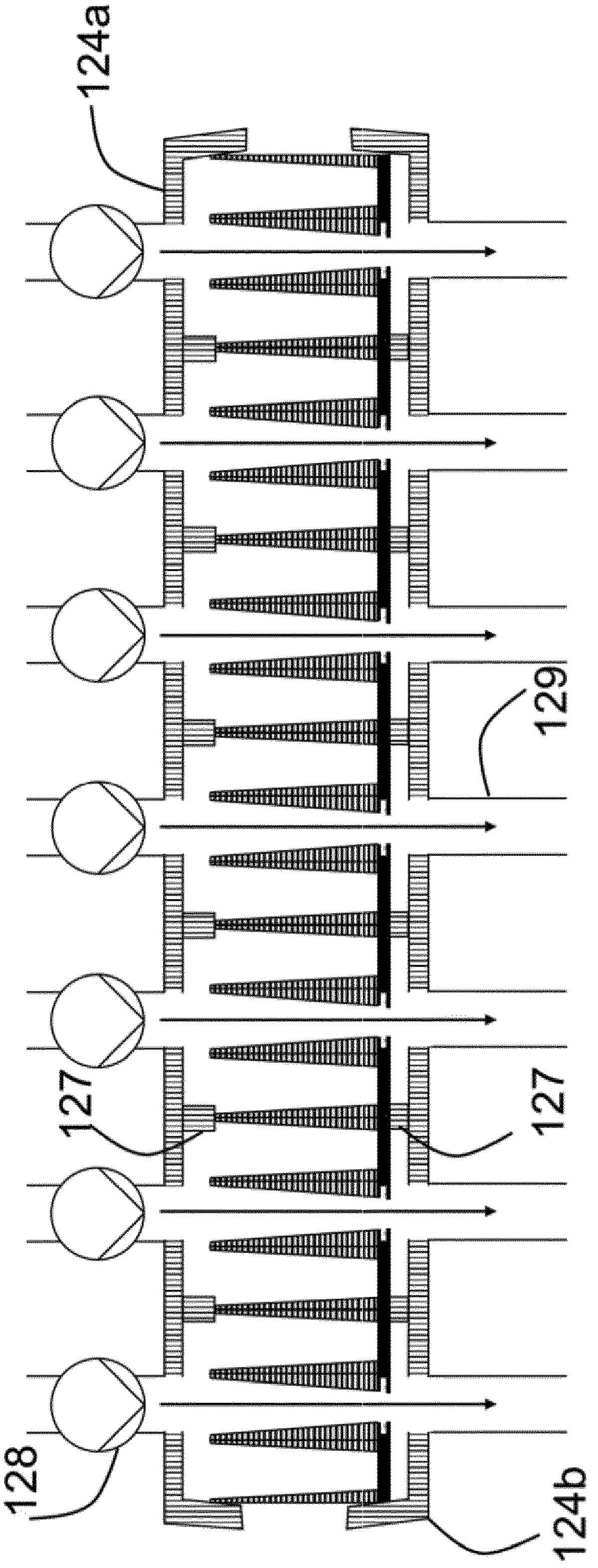
FIG. 18 shows an example microfluidic device with dedicated fluid inlets and dedicated fluid outlets.

FIGS. 15 to 17 show example devices with differing numbers of fluid inlets and outlets for the purposes of efficient multiplexing and demultiplexing of fluid streams. FIG. 18 shows an alternative configuration of device with each microfluidic network of the device completely isolated from other networks, with sealing members 127 provided on upper enclosure 124*a* and lower enclosure 124*b*. Each network is provided with a dedicated fluid inlet 128 and dedicated fluid outlet 129, i.e. there is a 1:1:1 ratio of conduit:inlet:outlet.

It will be understood that the devices depicted in the Figures are merely examples of how microfluidic cell culture devices of the present disclosure may be constructed, and that other configurations may be possible.

EXAMPLES

A microfluidic device in accordance with the example of FIGS. 1 to 3 was constructed with a base aperture diameter of 0.5 mm and a cover aperture diameter of 1 mm, and used in the following protocols:

Protocol 1

Step 1

- 2.5 μL of collagen 1 (a 8:1:1 mix of Collagen 1 5 mg/ml, Hepes and $NaHCO_3$, then diluted in HBSS to 3 mg/ml) was seeded into the support compartment via its media inlet.
- Gel is allowed to fill through the chamber where it is pinned by the apertures and capillary pressure barriers
- Gel is incubated for 10 min and HBSS is added to perfusion compartment Step 2

- A suspension of $5\text{-}10^6$/ml dissociated lung organoid in culture medium was seeded at volumes of 0,5 μl to the conduit and allowed to form a layer on the gel surface.
- Plate was placed at a 90° angle to allow sedimentation on one side of the conduit.

Microscopy analysis from above confirmed the presence of a meniscus at the base aperture indicating pinning, which was also confirmed with no sign of leakage into the base layer. The meniscus was visible in phase contrast due to the air liquid interface causing refraction of the light, making the meniscus appear black. Cell seeding on the ECM gel was also visible.

Protocol 2

Step1

- 2.5 μL of collagen 1 at 3 mg/ml seeded into the support compartment via its media inlet.
- Gel is allowed to fill through the chamber where it is pinned by the apertures and capillary pressure barriers
- Gel is incubated for 10 min and HBSS is added to perfusion compartment Step 2

- A suspension of $20^6$/ml Caco2 cells in culture medium was seeded at volumes of 0.3 μL to the conduit and allowed to form a layer on the gel surface.
- Two methods were tested.
  - Method 1: The plate was placed flat for 30 min. It was observed most cells did not settle on the ECM, so the plate was then flipped
- 50 μL of media was then added to the conduit in two steps of 25 μL with the lowest dispensing speed of the electronic pipette to avoid breaking the pinning at the bottom of the plate.

Media Removal—Airlifting

Plate from Protocol 2 was thoroughly emptied of all media using an aspirator without touching the base aperture (aspiration tip in the corner)·

Plate was placed upside down in the flow cabinet.

After a couple of minutes, it was observed that the conduit had been airlifted, but not dried in.

20 μL culture media was added to all side inlets and outlets to fill the perfusion compartments.

Figure 19A:
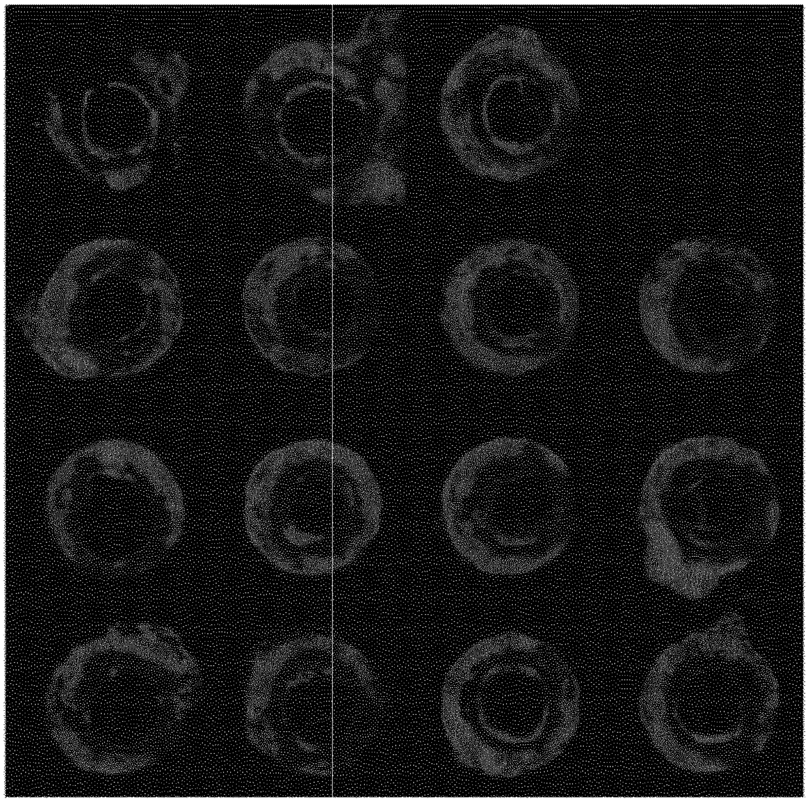
FIGS. 19A and 19B show confocal microscopy immunostaining images of seeded cells in a device as described herein.
Figure 19B:
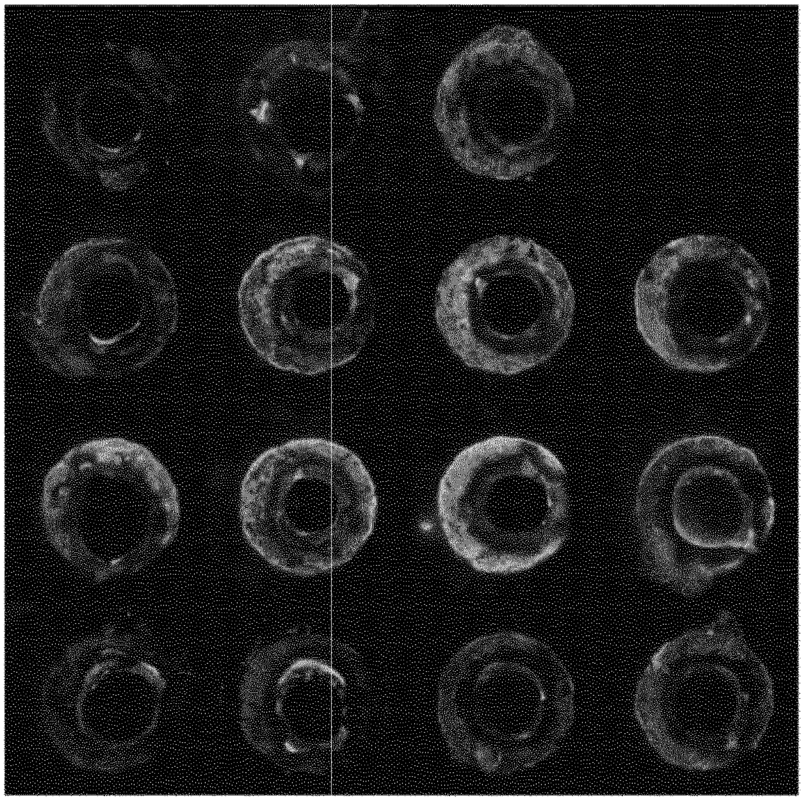

Plate was placed back in the incubator, on a rocker to allow media to perfuse through the ECM After 72 hours, all microfluidic networks that had been seeded and airlifted remained so. After 3 days of culturing, the cells were stained using Actin-Red (Thermofisher Scientific #R37112), confirming the presence of the CaCo2 cells in a tubule around the perimeter of the conduit. Images of the formed tube were made using confocal microscopy, representative examples of which are shown in FIGS. 19A and 19B.

Protocol 3

Step 1—Hydrogel Seeding 2.5 μL of 5 mg/ml collagen I was seeded into the support compartment via its media inlet.

Gel is allowed to fill through the chamber where it is pinned by the apertures and capillary pressure barriers.

Gel is incubated for 20 min and HBSS is added to perfusion compartment

Plates were stored at room temperature until use

Step 2—Cell Seeding

A suspension of $20 \cdot 10^6$/ml human bronchial epithelial cells (NHBE) in culture medium was seeded at volumes of 0.25 μl to the conduit and allowed to form a layer on the gel surface.

50 ul of medium was added to all perfusion channels and plate was placed at a 90° angle for 2 hours to allow sedimentation on one side of the conduit.

The plate was turned 180° and incubated on the other side for 2 hr.

50 ul of medium was added to conduit chamber (lowest speed on electronic multichannel)

Media Removal—Airlifting

Plate was emptied of all media using an aspirator without touching the base aperture.

Plate was placed upside down in the flow cabinet for about 3 min to let chip dry Checked under microscope whether airlift was established.

Figure 20:
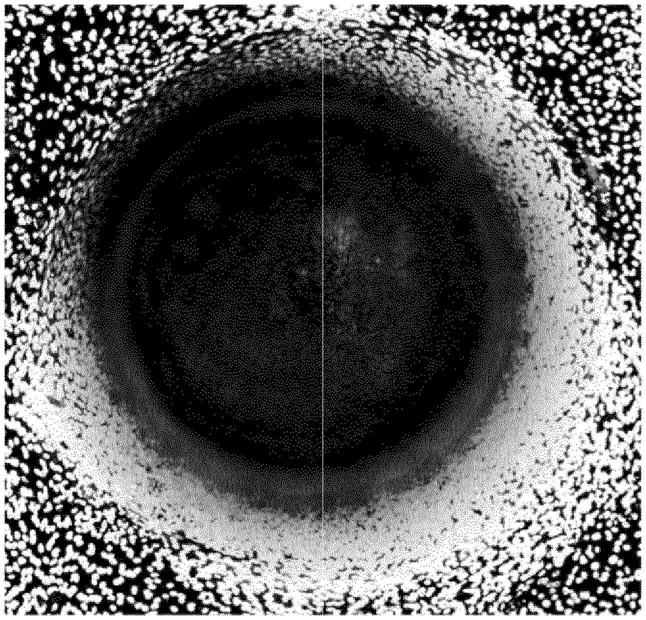
FIG. 20 shows a confocal microscopy DNA color coding image of seeded cells in a device as described herein.

50 μL culture media was added to all side inlets and outlets to fill the perfusion compartments Airlift was stable over time. After 28 days of culture the cultures were DNA color coded. Images of the formed tube were made using confocal microscopy and show a confluent cell layer against the hydrogel. A representative example is shown in FIG. 20.

The above description is for the purpose of teaching the person of ordinary skill in the art how to practice the present invention, and it is not intended to detail all those modifications and variations which will become apparent upon reading the description. It is intended, however, that all such modifications and variations be included within the scope of the present invention, which is defined by the following claims.

The invention claimed is:

1. A microfluidic cell culture device, comprising:

at least one microfluidic network, the microfluidic network comprising:

a base, a microfluidic channel, and a cover;

at least one perfusion compartment inside the microfluidic channel; and at least one support compartment inside the microfluidic channel; wherein the base and cover each comprise an aperture, thereby defining a conduit through the microfluidic channel; and the conduit is in fluidic communication with the at least one support compartment, and in fluidic communication with the at least one perfusion compartment through the at least one support compartment.

2. The microfluidic cell culture device of claim 1, wherein the conduit is substantially orthogonal to a plane of the microfluidic network.

3. The microfluidic cell culture device of claim 1, wherein:

the aperture in the base is substantially aligned with the aperture in the cover; the aperture in the base is substantially concentric with the aperture in the cover; and/or a diameter of the aperture in the base is smaller than a diameter of the aperture in the cover.

4. The microfluidic cell culture device of claim 1, wherein any one or both of the aperture in the base and the aperture in the cover has a rim which is configured to pin a fluid within the at least one support compartment.

5. The microfluidic cell culture device of claim 1, wherein the at least one support compartment is defined at least in part by any one or more of:

the aperture in the base;

the aperture in the cover; and one or more capillary pressure barriers located in the microfluidic channel.

6. The microfluidic cell culture device of claim 5, wherein one capillary pressure barrier of the one or more of the capillary pressure barriers defines at least in part a boundary between the at least one support compartment and the at least one perfusion compartment and/or wherein one capillary pressure barrier of the one or more capillary pressure barriers defines at least in part a boundary between the at least one support compartment and the conduit.

7. The microfluidic cell culture device of claim 1, wherein the at least one support compartment and/or the at least one perfusion compartment are each in fluidic communication with one or more respective inlets and/or one or more respective outlets; and/or wherein the at least one perfusion compartment and the at least one support compartment are adjacent one another and in the same plane in the microfluidic network.

8. The microfluidic cell culture device of claim 1, wherein the at least one support compartment does not include a membrane for supporting a layer of cells.

9. The microfluidic cell culture device of claim 1, wherein the microfluidic cell culture device comprises more than one fluidic inlet and more than one fluidic outlet, optionally wherein the number of fluidic inlets is different to the number of fluidic outlets.

10. The microfluidic cell culture device of claim 1, further comprising at least one enclosure that at least partially covers an exterior part of the base and/or the exterior part of the cover.

11. The microfluidic cell culture device of claim 10, wherein all or part of the at least one enclosure is removeable; and/or wherein the at least one enclosure comprises one or more of:

a port for fluid exchange, tubing for guiding the fluid flow, a window for optical access, a filter for exchanging fluid without contamination, and a tortuous path for exchanging gaseous fluids without contamination.

12. The microfluidic cell culture device of claim 10, wherein:

the at least one enclosure defines a connecting channel connecting the conduits of at least two microfluidic networks of the plurality of microfluidic networks via their respective apertures in the base; and/or the at least one enclosure defines a connecting channel connecting the conduits of at least two microfluidic networks of the plurality of microfluidic networks via their respective apertures in the cover.

13. The microfluidic cell culture device of claim 11, wherein the at least one enclosure comprises one or more fluid inlets and/or fluid outlets, optionally wherein the enclosure is connected to a positive or negative pressure source.

14. The microfluidic cell culture device of claim 13, wherein the one or more fluid inlets are connected to the one or more fluid outlets outside of the microfluidic network, optionally through a pump, thereby enabling an at least partially circulating flow.

15. The microfluidic cell culture device according to claim 5, wherein the one or more capillary pressure barriers each comprise:

a ridge of material protruding from an internal surface of the microfluidic channel;

a widening of the microfluidic channel;

a groove in an internal surface of the microfluidic channel;

a region of material of different wettability to an internal surface of the microfluidic channel; or a plurality of pillars at regular intervals.

* * * * *